(12) United States Patent
Kizuka et al.

(10) Patent No.: US 10,398,552 B2
(45) Date of Patent: Sep. 3, 2019

(54) FIXATION DEVICES, SYSTEMS AND METHODS FOR HEART VALVE LEAF REPAIR

(71) Applicant: Abbott Cardiovascular Systems Inc., Santa Clara, CA (US)

(72) Inventors: Koji J. Kizuka, San Francisco, CA (US); Michael Z. Chong, San Francisco, CA (US)

(73) Assignee: Abbott Cardiovascular Systems Inc., Santa Clara, CA (US)

(*) Notice: Subject to any disclaimer, the term of this patent is extended or adjusted under 35 U.S.C. 154(b) by 0 days.

(21) Appl. No.: 15/352,337

(22) Filed: Nov. 15, 2016

(65) Prior Publication Data

US 2018/0133008 A1    May 17, 2018

(51) Int. Cl.
| | |
|---|---|
| *A61F 2/24* | (2006.01) |
| *A61B 17/00* | (2006.01) |
| *A61B 17/29* | (2006.01) |
| *A61B 17/122* | (2006.01) |
| *A61B 17/128* | (2006.01) |

(52) U.S. Cl.
CPC ...... *A61F 2/2442* (2013.01); *A61B 17/00234* (2013.01); *A61B 17/122* (2013.01); *A61B 17/1285* (2013.01); *A61B 17/29* (2013.01); *A61F 2/2463* (2013.01); *A61B 2017/00243* (2013.01); *A61B 2017/00292* (2013.01); *A61B 2017/2946* (2013.01)

(58) Field of Classification Search
CPC ..................................................... A61B 17/03
USPC ......................................................... 600/37
See application file for complete search history.

(56) References Cited

U.S. PATENT DOCUMENTS

| | | | |
|---|---|---|---|
| 3,671,979 A | 6/1972 | Moulopoulos | |
| 3,874,338 A | 4/1975 | Happel | |
| 4,056,854 A | 11/1977 | Boretos et al. | |
| 4,484,579 A | 11/1984 | Meno et al. | |
| 4,917,089 A | 4/1990 | Sideris | |
| 4,994,077 A | 2/1991 | Dobben | |
| 5,332,402 A | 7/1994 | Teitelbaum | |
| 5,411,552 A | 5/1995 | Andersen et al. | |
| 5,554,185 A | 9/1996 | Block et al. | |
| 5,662,681 A * | 9/1997 | Nash ................. | A61B 17/0057 604/285 |
| 5,718,725 A | 2/1998 | Sterman et al. | |
| 5,769,812 A | 6/1998 | Stevens et al. | |

(Continued)

FOREIGN PATENT DOCUMENTS

| | | |
|---|---|---|
| CN | 202859228 U | 4/2013 |
| WO | WO 91/01689 A1 | 2/1991 |

(Continued)

OTHER PUBLICATIONS

European Patent Office, International Search Report, dated Jan. 31, 2018, pp. 1-5

*Primary Examiner* — Yashita Sharma
(74) *Attorney, Agent, or Firm* — Baker Botts L.L.P.

(57) ABSTRACT

Devices, systems and methods for repairing a valve in a patient's heart includes a two or more fixations devices, each fixation device being attachable to the free end of a target tissue, such as a valve leaflet, the fixation devices being coupled together by a coupling device capable of repositioning and coupling the fixation devices in order to reposition the free ends of the valve leaflets.

15 Claims, 18 Drawing Sheets

(56) References Cited

U.S. PATENT DOCUMENTS

| | | |
|---|---|---|
| 5,797,960 A | 8/1998 | Stevens et al. |
| 5,823,956 A | 10/1998 | Roth et al. |
| 5,829,447 A | 11/1998 | Stevens et al. |
| 5,840,081 A | 11/1998 | Andersen et al. |
| 5,855,614 A | 1/1999 | Stevens et al. |
| 6,461,366 B1 | 10/2002 | Seguin |
| 6,629,534 B1 | 10/2003 | Goar St. et al. |
| 6,695,866 B1 | 2/2004 | Kuehn et al. |
| 6,719,767 B1 | 4/2004 | Kimblad |
| 6,752,813 B2 | 6/2004 | Goldfarb et al. |
| 7,112,207 B2 | 9/2006 | Allen et al. |
| 7,288,097 B2 | 10/2007 | Séguin |
| 7,464,712 B2 | 12/2008 | Oz et al. |
| 7,513,908 B2 | 4/2009 | Lattouf |
| 7,563,267 B2 | 7/2009 | Goldfarb et al. |
| 7,569,062 B1 | 8/2009 | Kuehn et al. |
| 7,604,646 B2 | 10/2009 | Goldfarb et al. |
| 7,811,296 B2 | 10/2010 | Goldfarb et al. |
| 7,914,544 B2 | 3/2011 | Nguyen et al. |
| 8,029,565 B2 | 10/2011 | Lattouf |
| 8,052,592 B2 | 11/2011 | Goldfarb et al. |
| 8,216,256 B2 | 7/2012 | Raschdorf, Jr. et al. |
| 8,425,504 B2 | 4/2013 | Orton et al. |
| 8,496,671 B1 | 7/2013 | Hausen |
| 8,961,594 B2 | 2/2015 | Maisano et al. |
| 9,572,666 B2 | 2/2017 | Basude et al. |
| 2003/0018358 A1* | 1/2003 | Saadat ............... A61B 17/0401 606/232 |
| 2004/0044350 A1 | 3/2004 | Martin et al. |
| 2004/0049207 A1 | 3/2004 | Goldfarb et al. |
| 2007/0038293 A1 | 2/2007 | Goar St. et al. |
| 2007/0197858 A1 | 8/2007 | Goldfarb et al. |
| 2010/0022823 A1* | 1/2010 | Goldfarb ............ A61B 17/0401 600/37 |
| 2013/0066341 A1 | 3/2013 | Ketai et al. |
| 2016/0157862 A1 | 6/2016 | Hernandez et al. |

FOREIGN PATENT DOCUMENTS

| | | |
|---|---|---|
| WO | WO 98/35638 A1 | 8/1998 |
| WO | WO 99/00059 A1 | 1/1999 |
| WO | WO 99/01377 A1 | 1/1999 |
| WO | WO 00/03759 A2 | 1/2000 |
| WO | WO 00/60995 A2 | 10/2000 |
| WO | WO 2004/103162 A2 | 12/2004 |
| WO | WO 2006/037073 A2 | 4/2006 |
| WO | 20120087842 A1 | 6/2012 |

* cited by examiner

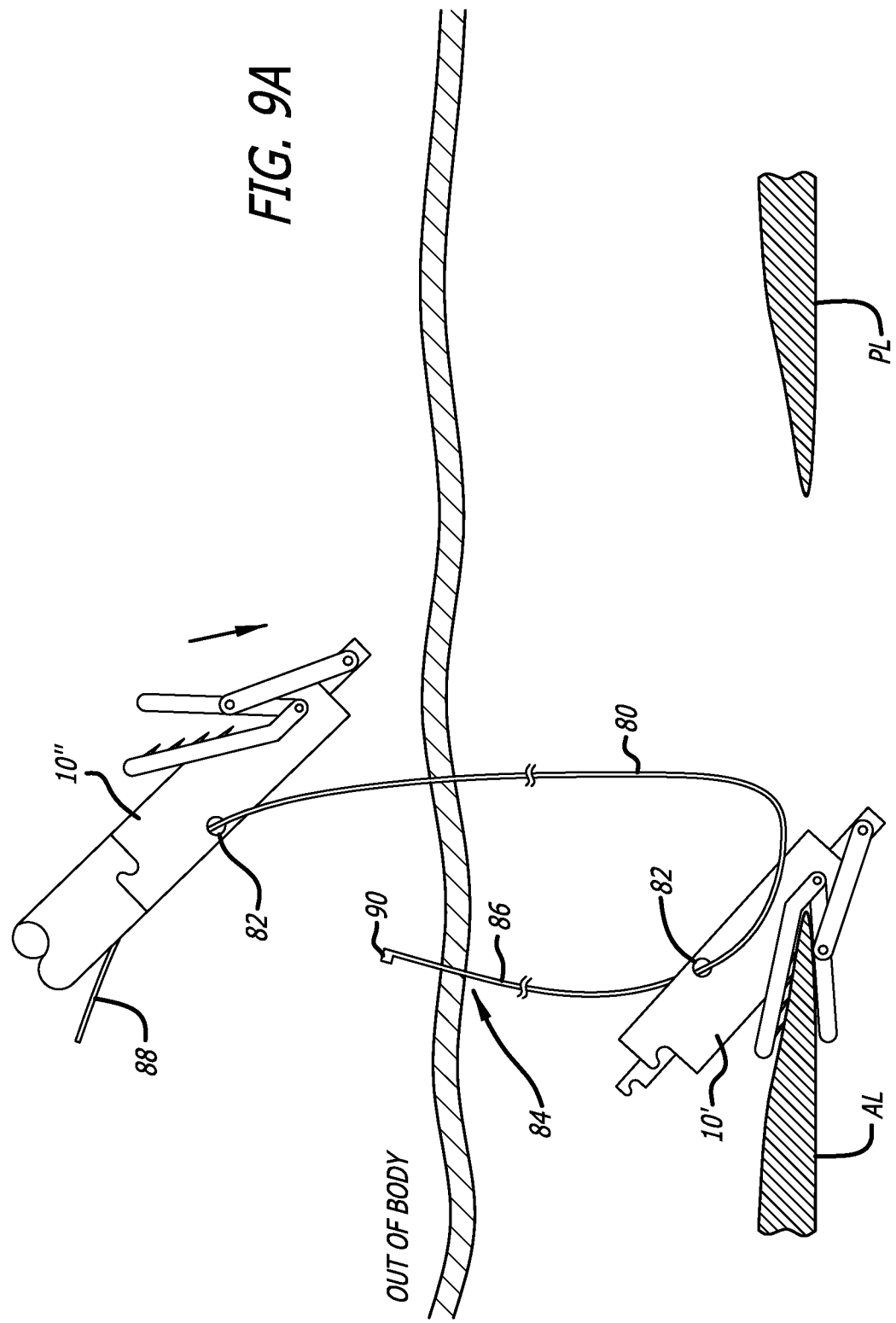

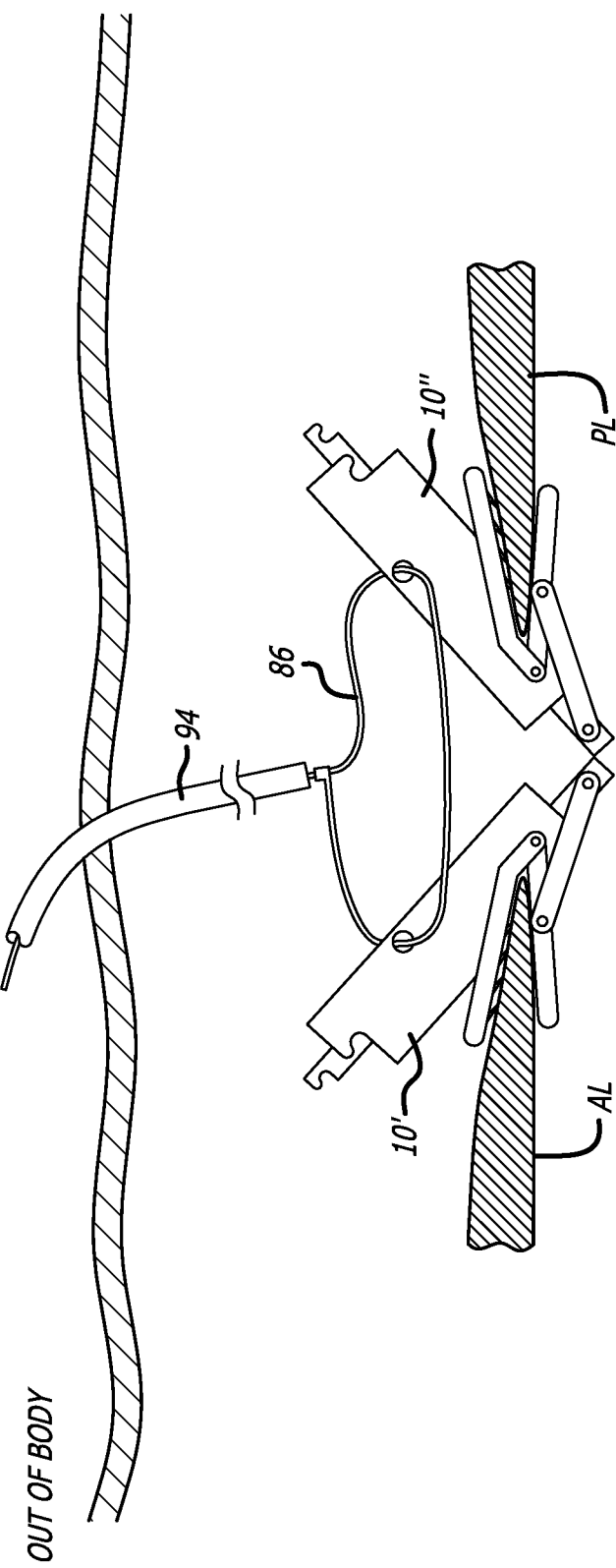

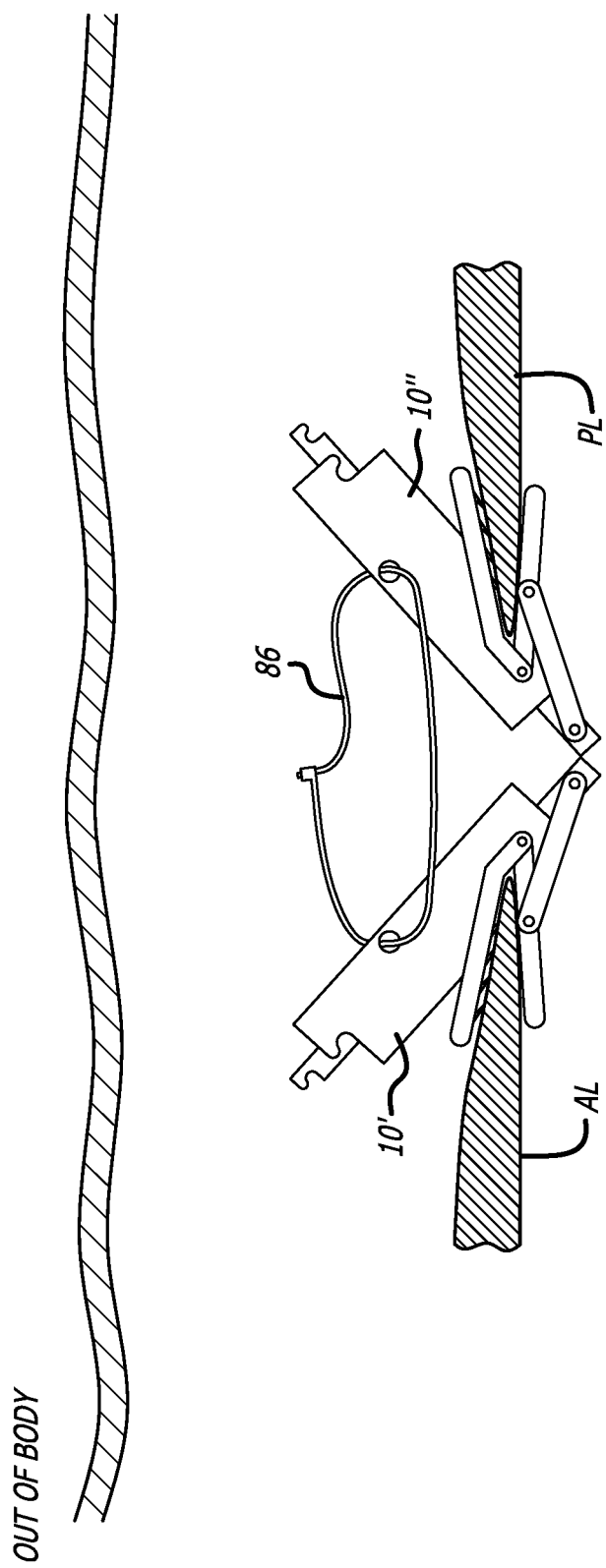

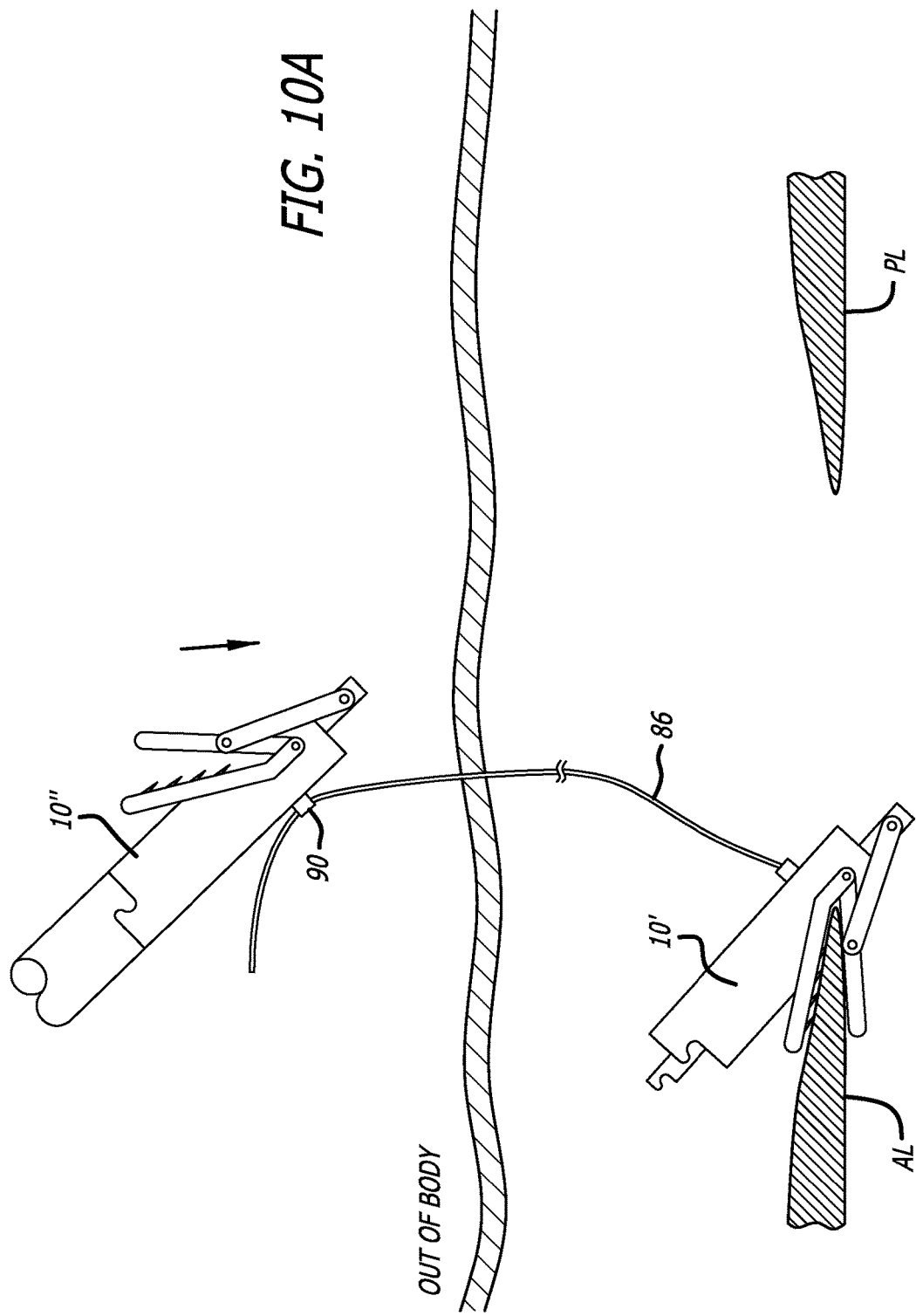

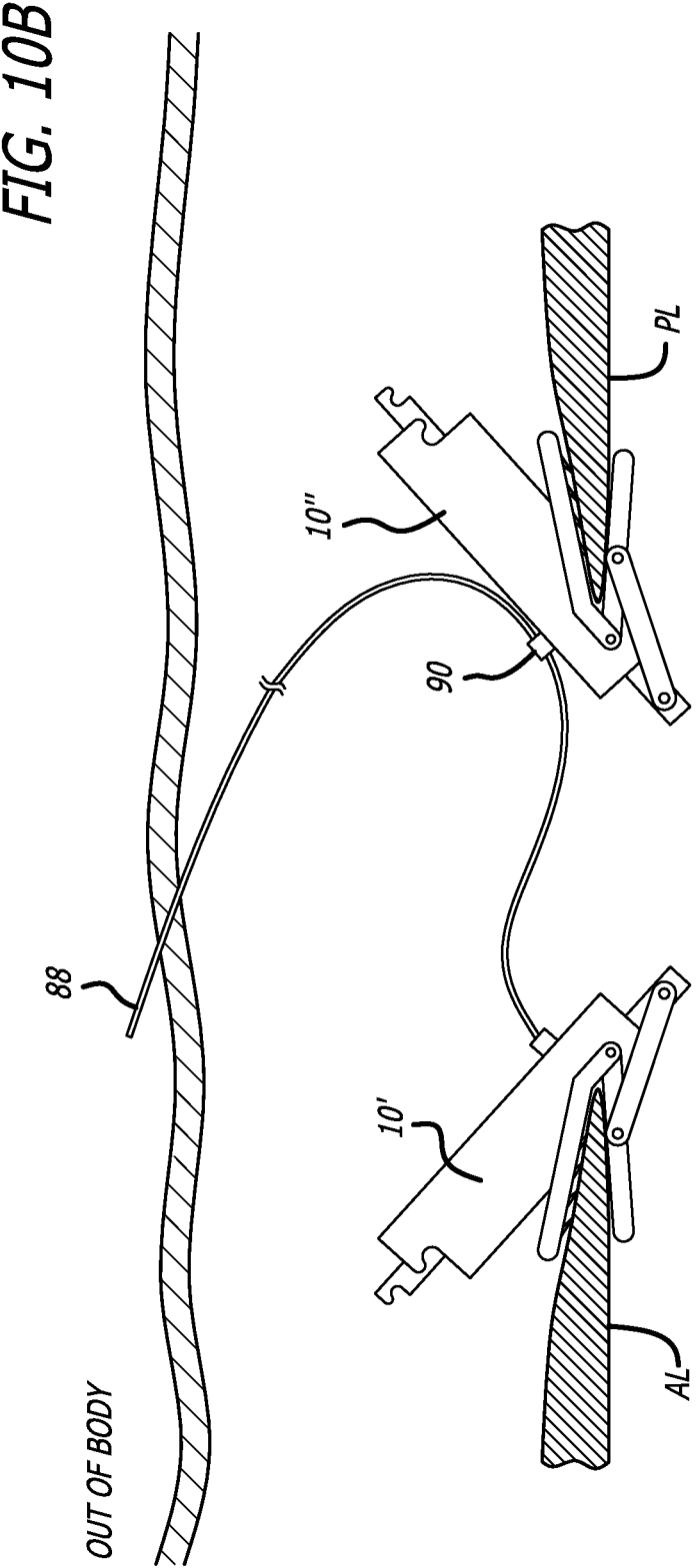

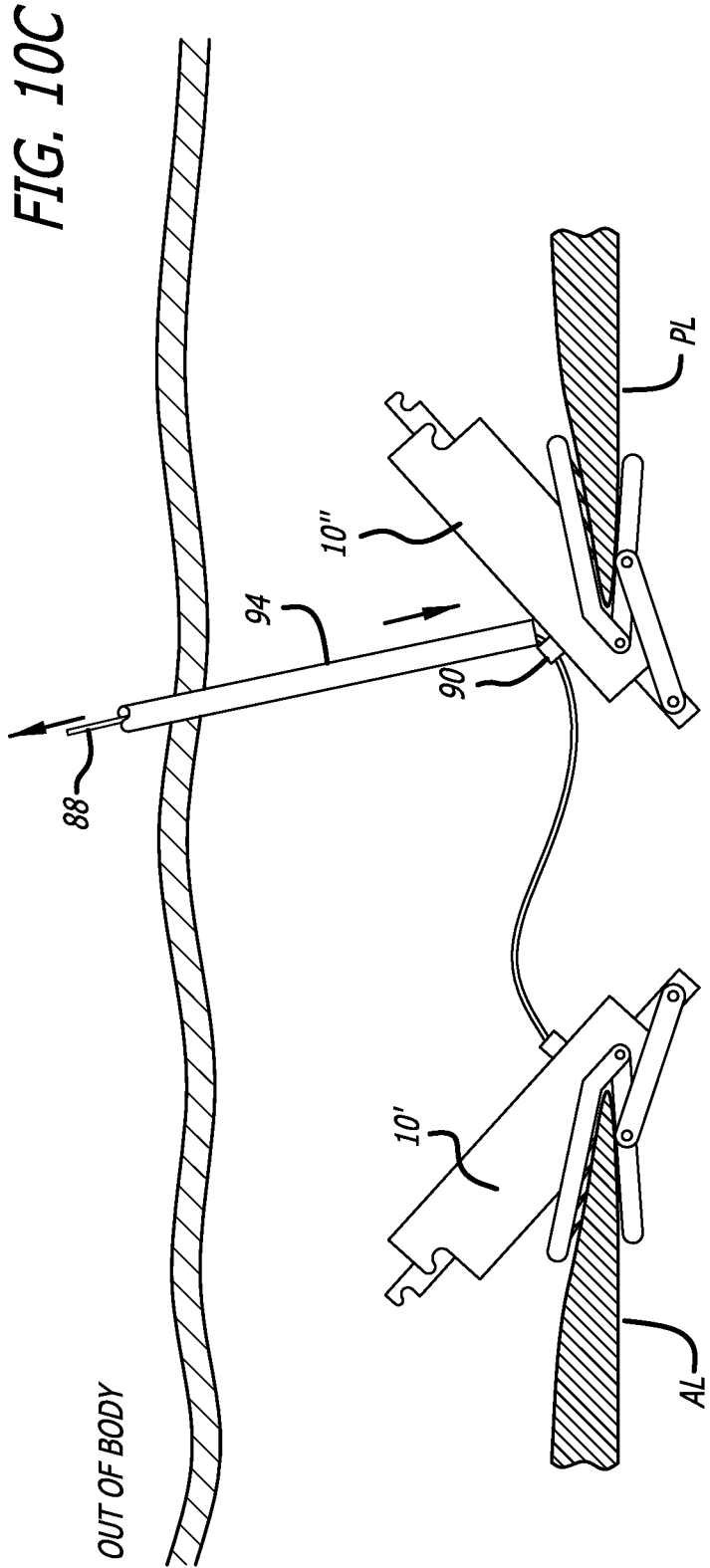

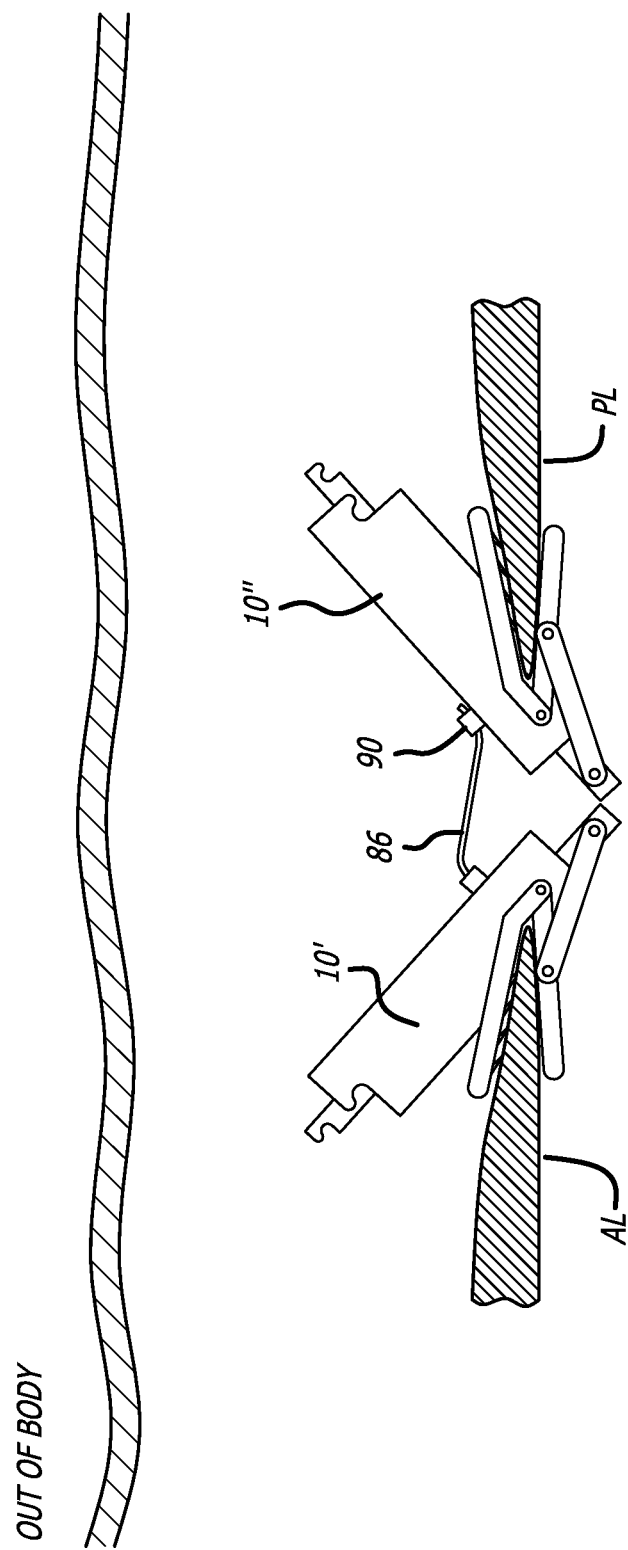

*FIG. 11A*
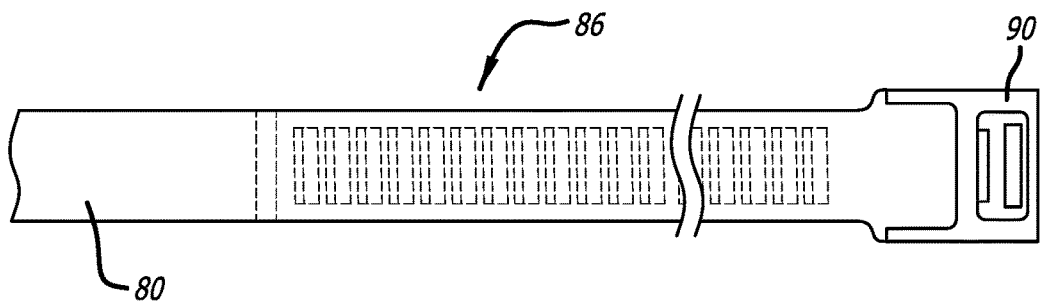
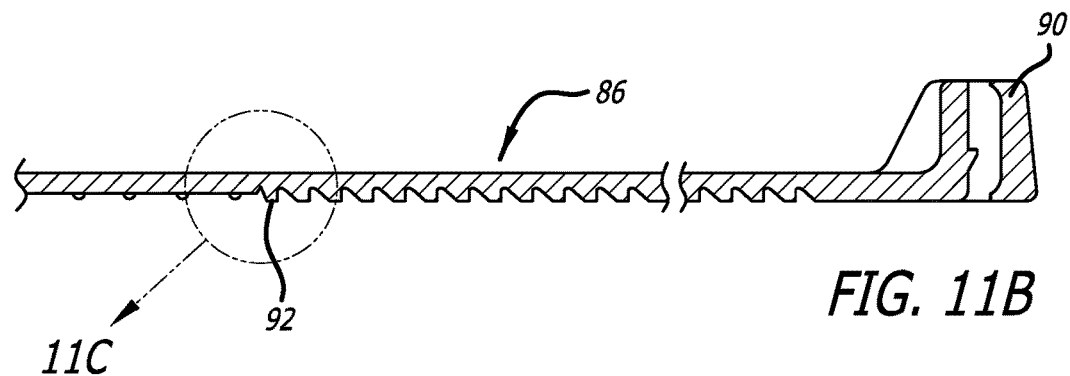
*FIG. 11B*
*FIG. 11C*
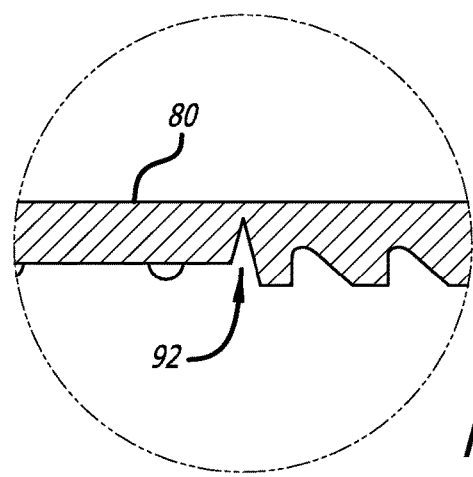

FIXATION DEVICES, SYSTEMS AND METHODS FOR HEART VALVE LEAF REPAIR

BACKGROUND

The present invention relates generally to medical methods, devices, and systems for the endovascular, percutaneous or minimally invasive surgical treatment of bodily tissues, such as tissue approximation or valve repair. More particularly, the present invention relates to repair of valves of the heart and venous valves.

Surgical repair of bodily tissues often involves tissue approximation and fastening of such tissues in an approximated arrangement. Tissue approximation includes coapting the leaflets of the valves in a therapeutic arrangement which may then be maintained by fastening or fixing the leaflets via the use of an implanted fixation device. Such coaptation can be used to treat regurgitation which most commonly occurs in the mitral valve and tricuspid valve of the human heart.

During normal operation of the heart, the valve leaflets of the mitral valve open during diastole when the left atrium of the heart is filled with blood allowing the blood to pass into the left ventricle. During a normal cycle of heart contraction (systole), the valve leaflets are pushed together such that the free edges of the leaflets are closed against each other along a line of coaptation to prevent the back-flow or "regurgitation" of blood into the left atrium. In this fashion, the mitral valve functions as a "check valve" or "one-way valve" which closes the opening of the valve to prevent back-flow of oxygenated blood into the left atrium when the pressure developed in the left ventricle exceeds the pressure in the left atrium. In this way, oxygenated blood can be effectively pumped from the left ventricle into the aorta through the aortic valve. Regurgitation can significantly decrease the pumping efficiency of the heart, placing the patient at risk of severe, progressive heart failure.

The mitral valve leaflets are attached to the surrounding heart structure along an annular region referred to as the valve annulus. The free edges of the leaflets are secured to the lower portions of the left ventricle through tendon-like tissue structures known as chordae tendineae or chordae. The chordae are attached to the papillary muscles which extend upwardly from the lower portions of the left ventricle and interventricular septum.

Mitral valve regurgitation can result from a number of different mechanical defects in the mitral valve or the left ventricular wall. The valve leaflets, the valve chordae which connect the leaflets to the papillary muscles, the papillary muscles or the left ventricular wall may be damaged or otherwise dysfunctional. Commonly, the valve annulus may be damaged, dilated, or weakened, limiting the ability of free ends of the leaflets of the mitral valve to close adequately against each other due to the high fluid pressures that can develop in the left ventricle during systole.

Common treatments for mitral valve regurgitation rely on valve replacement or repair of damaged leaflets, along with annulus remodeling which is generally referred to as valve annuloplasty. Additional techniques for mitral valve repair rely on suturing adjacent segments of the opposed valve leaflets together and is referred to as the "bow-tie" or "edge-to-edge" technique. While all these techniques can be very effective, they usually rely on open heart surgery where the patient's chest is opened, typically via a sternotomy, and the patient placed on cardiopulmonary bypass. The need to both open the chest and place the patient on bypass is traumatic and has associated high mortality and morbidity.

Accordingly, successful methods have been developed for performing less invasive repairs to the mitral valve in order to avoid the open heart procedure. Such repair procedures also can be performed on a beating heart such that the patient does not have to be placed on cardiopulmonary bypass.

These less invasive procedures for mitral valve repair rely on the introduction of instruments via a transcatheter procedure in which an opening is made into the wall of heart that allows the instruments to enter the heart, usually in the left or right atrium. Suitable gripping and fastening instruments have appropriate dimensions to fit through a cardiac guide catheter into the heart. The methods of repair of the mitral valve typically include gripping the edges of the two leaflets of the mitral valve, and securing them together using clasping, stitching, or suturing techniques. The free ends of the leaflets of the mitral valve also could be secured together utilizing a repair device which remains permanently implanted inside the atrium of the patient. Such a repair device shall be referred to hereinafter as a "fixation device." The connection of the leaflets of the mitral valve together over a short length reduces the loss of tension in the leaflets thus allowing the remaining portions of the leaflets to have better coaptation and better perform the function of a one-way valve by preventing or reducing blood flow in the wrong direction.

Tricuspid valve prolapse, i.e. degeneration of tricuspid valve leaflets, is the most common cause of tricuspid regurgitation in North America. Many cases of regurgitation can be repaired by modifications of the original valve using a valvuloplasty procedure. However, valves that are heavily calcified or significantly compromised by disease may need to be replaced. The same approach taken in repairing the mitral valve has been tried for repairing the tricuspid valve using clasps such as the MitraClip® clasp, manufactured and sold by Abbott Vascular, Santa Clara, Calif. The tricuspid valve is similar to the mitral valve, hut it is more complex in that it has three leaflets, namely, the anterior leaflet, posterior leaflet and septal leaflet, which all converge at a common point of meeting near the center of the valve. The tricuspid valve prevents back flow of blood from the right ventricle into the right atrium during ventricular systole when it closes and allows blood to flow from the right atrium into the right ventricle during ventricular diastole when it opens. This valve can be weakened, for example, by drug abuse, endocarditis, rheumatic fever, heart disease and congenital abnormality. Tricuspid regurgitation, like mitral regurgitation, is typically caused by defective coaptation of the leaflets of the valve against each other and results in reduced pumping efficiency. Diagnosis of tricuspid regurgitation can be performed using visualization with transesophageal echocardiography or by echocardiography. In particular, defective leaflet coaptation and the site and direction of the regurgitant flow can be examined to evaluate likely modes of failure.

Methods for repairing the mitral valve normally do not apply conveniently to a method for repairing the tricuspid valve. One major difference is that while the mitral valve has only two leaflets extending generally parallel with each other and which need to be grasped simultaneously, the tricuspid valve has three leaflets that come to a common point of meeting. The mechanical problems involved in grasping all three leaflets simultaneously at a single point are far more complex than with the mitral valve because the operator is not presented with two elongated edges to grasp, but rather, with three triangulated points that must be grasped simultaneously. However, an interventionalist successfully performing this procedure can increase the tension in the leaflets to improve coaptation of the leaflets and help reduce regurgitation.

As used herein, the term "endovascular," refers to procedure(s) of the present invention that are performed with interventional tools and supporting catheters and other equipment introduced to the heart chambers from the patient's arterial or venous vasculature remote from the heart. The interventional tools and other equipment may be introduced percutaneously, i.e., through an access sheath, or may be introduced via a surgical cut down, and then advanced from the remote access site through the vasculature until they reach the heart. In some instances, penetrations will be made interior to the heart, e.g., through the interatrial septum to provide a desired access route for the vascular instruments.

For these reasons, it would be desirable to provide alternative and additional methods, devices, and systems for performing the repair of mitral valves and other cardiac valves, such as the tricuspid valve, along with venous valves. Such methods, devices, and systems should preferably not require open chest access and be capable of being performed either endovascularly, i.e., using devices which are advanced to the heart from a point in the patient's vasculature remote from the heart or by a minimally invasive approach. Still more preferably, the methods, devices, and systems would be useful if the leaflets of the valve did not have to be grasped simultaneously by the fixation device. Additionally, it would be beneficial if two or more of the target tissue could be grasped by the fixation device at different locations which are not necessarily adjacent to each other but can nevertheless be drawn together to meet at or near a common location to close the gap formed on a damaged valve. Further, such devices and systems should provide features which allow repositioning and optional removal of the fixation device before the fixation device is permanently secured to the leaflets to ensure optimal placement. The present invention addresses these, and other needs.

SUMMARY OF THE INVENTION

The present invention provides devices, systems and methods for tissue approximation and repair at treatment sites. The devices, systems and methods of the invention can be used in a variety of therapeutic procedures, including endovascular, minimally-invasive and can be used in various anatomical regions. The invention is particularly useful in those procedures requiring minimally-invasive or endovascular access to remote tissue locations, where the instruments utilized must negotiate long, narrow, and tortuous pathways to the treatment site.

In preferred embodiments, the devices, systems and methods of the invention are adapted for fixation of tissue at a treatment site utilizing minimally invasive procedures by advancing catheters into the heart location, rather than utilizing an open heart procedure. In a particularly preferred embodiment, the devices, systems and methods of the invention are adapted for repair of cardiac valves, and particularly the mitral valve and tricuspid valve, as a therapy for regurgitation. The invention enables two or more valve leaflets to be coapted using an "edge-to-edge" or "bow-tie" technique to reduce regurgitation, yet does not require open surgery through the chest and heart wall as in conventional approaches. Using the devices, systems and methods of the invention, the mitral valve, for example, can be accessed from a remote surgical or vascular access point and the two valve leaflets may be coapted using endovascular or minimally invasive approaches. While less preferred, in some circumstances the invention may also find application in open surgical approaches as well.

The devices, systems and methods of the present invention are centered on the use of at least two separate fixation devices which grasp and position different portions of target tissue in order to alter the physiological positioning of the target tissue. In such a manner, gaps formed between normally adjacent tissue structure can be reduced or eliminated by initially attaching a first fixation device to one of the targeted tissue and then attaching a second fixation to a second target tissue. In another aspect, additional fixation devices could be further utilized if additional target tissue is needed to be grasped. These two or more fixations devices are coupled to each other which allows the interventionalist to re-position the fixation devices relative to each other which, in turn, manipulates or re-positions the target tissue which are gripped or grasped by each fixation device. For example, the present invention can be used to reduce the size of a gap formed between the free ends of the posterior leaflet and anterior leaflet of the mitral valve to minimize regurgitation. Initially, a first fixation device is inserted into the left atrium and is actuated to physically grasp the free end of either the posterior or anterior leaflet of the mitral valve. Another fixation device is then advanced into the left atrium and is attached to the other leaflet. The two or more fixation devices have an associated coupling device/system which couples the fixation devices together and which can be used to move each fixation in closer proximity to one another in vivo. As a result, the target tissue can be drawn closer to each other allowing the valve leaflets to better coapted using a modified "edge-to-edge" or "bow-tie" technique. Accordingly, any space or gap formed between the damaged leaflets of the heart valve can be reduced causing the damaged valve to function more like a normal valve which reduces unwanted regurgitation.

In these preferred embodiments, the present invention allows each leaflet to be grasped individually, eliminating the need to capture both leaflets simultaneously using a single fixation device, as is presently used in systems employing "edge-to-edge" or "bow-tie" techniques. Additionally, the use of individual fixation devices to grasp the target tissue allows the interventionist to grasp the target tissue at a location which might not directly across from the other target tissue. In other words, the target tissue to be grasped by each fixation device need not be located directly across from the other target tissue, which is usually required when utilizing a single fixation clip system. For example, one fixation device could be used to grasp target tissue located some distance away from the other target tissue. Since the fixation devices remain coupled to each other, the associated coupling device/system of the present invention allows the fixation devices to be drawn closer together after being initially attached to the respective target tissue irrespective of the fixation devices' initial location. Accordingly, the devices can be moved or drawn towards each other allowing the target tissue to be simultaneously drawn closer together thus reducing the size of any gap formed between the leaflets of the valve. These features are particularly useful when repairing a tricuspid valve since it is often difficult to grasp all three leaflets simultaneously using a single fixation device, as is currently being implemented in conventional repair systems.

In preferred embodiments, the interventional system includes a coupling device and system, mentioned above, for coupling the fixation devices and positioning the fixation devices relative to each other in vivo. Particular aspects of the coupling device/system are discussed in greater detail below. Additionally, the fixation device can be delivered to the target site utilizing an interventional system that includes a multi-catheter delivery system having a delivery catheter for each fixation device to be deployed. The components of the catheter delivery system will be discussed in greater detail below.

In an exemplary embodiment, the invention provides a fixation device including a stud and a pair of gripping elements (first and second gripping elements) for engaging tissue which are operatively coupled to the stud, each gripping element having a first end and a free end opposite the first end. The first and second gripping elements are moveable between a first open position wherein the free ends of the gripping elements are spaced apart and a second closed position wherein the free ends of the gripping elements are spaced close together to engage or "grip" the tissue. Preferably, the gripping elements are sufficiently spaced apart in the first open position to allow the target tissue to be positioned between the first and second gripping elements and are then brought much closer together to engage or grip the tissue. The gripping elements are movable to positions between the first open position and the second closed position to allow the gripping elements to grip tissue having different thicknesses. In this regard, the ability of the gripping elements to move to various positions allows the space between the gripping elements to be varied which allows the gripping elements to grasp tissue having different thicknesses.

In another aspect, the fixation device may further include an actuation mechanism for moving one or both of the first and second gripping elements between the first open position and the second closed position, and positions in between. A variety of actuation mechanisms may be used. In an exemplary embodiment, the second gripping element is connected with the actuating mechanism and pivots as the stud of the fixation device is moved relative to the gripping elements. The first gripping element could remain stationary as the actuating mechanism is moved. In such an embodiment, the fixation device utilizes a "push/pull" arrangement to move the stud and the position the second gripping element relative to the first gripping element. Such an actuating mechanism would include one or more link members connected to the second gripping element and the movable stud, whereby the sliding action of the stud relative to the grasping elements causes the link members to move (for example, via a pivoting action) the second gripping member. The pivoting of the second gripping element relative to the first gripping member causing the elements to move either towards or away from each other. Accordingly, the sliding motion of the stud can be in either direction to cause the second gripping member to move towards or away from the first gripping member.

In a preferred embodiment, the fixation device further includes a locking element operably associated with the sliding stud for locking the first gripping element and second gripping element in the first open position, the second closed position, or positions therebetween. Because the ideal degree of closure of the fixation device may not be known until it is actually applied to the target tissue, the locking mechanism is configured to retain the first and second gripping elements in position regardless of how open or closed they may be. Accordingly, depending upon the thickness of the target tissue, the particular position in which the first and second gripping elements successful grasp and lock the target tissue can vary. For this reason, a variety of locking positions may be implemented to provide a greater range of locking positions for the gripping elements. While a variety of locking mechanisms may be used, in an exemplary embodiment, the locking mechanism comprises one or a plurality of outwardly extending locking projections formed on the sliding stud which are adapted to engage one or more compatible recesses formed on a mounting body which carries the gripping elements and actuating mechanism. These locking projections, which act much like detents, move with the sliding stud and enter the compatible recesses formed on the mounting body to prevent the stud from moving unless the interventionalist desires to reposition the fixation device to a different location. A certain amount of actuating force is required to move the slidable stud to a new position since the outward projecting members are designed to engage the recesses until a sufficiently strong actuating force is exerted on the stud. Once the fixation device is in place, the locking mechanism will maintain the gripping elements in their respective position to maintain the necessary force to grasp and position the target tissue.

The gripping elements may be configured to provide high retention force so that the fixation device remains securely fastened to the target tissue throughout the cardiac cycle. At the same time, these gripping elements should be configured to minimize trauma to the tissue engaged by them. This allows the fixation device to be removed from the tissue after initial application without creating clinically significant injury to the tissue. In order to enhance retention without creating significant trauma, the gripping elements may have friction-enhancing features on their surfaces that engage the target tissue. Such friction-enhancing features may include barbs, bumps, grooves, openings, channels, surface roughening, coverings, and coatings, among others. Preferably the friction-enhancing features and the magnets will be configured to increase the retention force of the gripping elements on the target tissue, while not leaving significant injury or scarring if the fixation device is removed. The gripping elements may further have a shape and flexibility to maximize retention force and minimize trauma to the target tissue. The gripping elements may also be somewhat flexible so that they deflect to some degree in response to forces against the tissue engaged thereby, reducing the chances that the tissue will tear or bruise in response to such forces.

The fixation devices of the invention preferably are associated with a coupling device/system which allows any number of fixation devices to be coupled to each other at the site of the target tissue. In this regard, the coupling device/system of the present invention not only couples the various fixation devices together, but also provides a device/system for drawing the fixation devices closer to each other once the device is attached to the target tissue. Again, such a coupling device/system allows multiple fixation devices to be utilized, eliminating the need for the interventionalist to grasp all of the target tissue simultaneously with a single fixation device. The present invention further allows fixation devices to be attached to non-adjacent target tissue since the coupling device/system can be used to draw each fixation device in close proximity to each other.

In one particular embodiment, the coupling system includes a coupling wire that includes a distal coupling device with a locking component which is detachably coupled to the coupling wire and will remain implanted with the fixation devices within the patient. In one aspect of the invention, the coupling wire may be a separate flexible filament extending from one fixation device to the other(s) devices and which functions much like a "lasso" to couple the various devices together. In this manner, each fixation device includes a component, usually an opening or port created on the body of the fixation device, which receives the coupling wire and its distal coupling device. In use, the coupling wire engages with each fixation device and is retracted to draw the fixation devices closer to each other using, for example, a lasso technique. The size of the lasso becomes smaller as the coupling wire is retracted which causes the fixation devices to be drawn in closer proximity to one another. Once the fixation devices have been properly positioned on the respective target tissues, the interventionalist can then break the coupling wire along a frangible connector which is disposed between the distal coupling device and the remainder of the coupling wire. When the frangible connector breaks, the coupling device remains affixed to the fixation devices since the remainder of the coupling wire will break free from the coupling device. The remainder of the coupling wire can be removed from the patient allowing the coupling device to remain engaged with the fully deployed fixation devices.

As is mentioned above, the fixation devices are designed to be detached from the coupling wire to allow the devices to be permanently implanted in the patient. In such applications, it is often desirable to promote tissue growth around the fixation device. For this purpose, some or all of the components of the fixation device are preferably covered with a covering or coating to promote tissue growth. In one embodiment, a biocompatible fabric cover can be positioned over the distal elements and/or the proximal elements. The cover may optionally be impregnated or coated with various therapeutic agents, including tissue growth promoters, antibiotics, anti-clotting, blood thinning, and other agents. Alternatively or in addition, some or all of the fixation element and/or covering may be comprised of a bioerodable, biodegradable or bioabsorbable material so that it may degrade or be absorbed by the body after the repaired tissues have grown together.

The fixation device is preferably delivered to a target location in a patient's body by a delivery system which includes a catheter having an elongated shaft, a proximal end and a distal end, the delivery catheter being configured to be positioned at the target location from a remote access point such as a vascular puncture or a cut-down or a surgical penetration. The fixation device is preferably delivered via the delivery system in a delivery position which is configured to minimize the profile of the fixation device.

In another aspect of the present invention, the delivery catheter for delivering and advancing the fixation device into the target site is configured to detachably connect an inner actuator rod to the slidable stud of the fixation device and includes an outer catheter member which is detachable connected to a mounting body of the fixation device. The actuator rod is designed to slide and extend within a lumen of the other catheter member and is interconnected to the sliding stud inn order to remotely position the stud in order to achieve the desired locking position for the gripping elements. In one particular embodiment, the gripping elements and actuating mechanism are mounted to the mounting body which may be in the form of a tubular component having a lumen adapted to receive the slidable stud. The actuator rod includes a distal end having a mating junction with the slidable stud. Likewise, the outer catheter member include a similar mating junction at its distal end which mates with the mounting body of the fixation device. In use, the actuator rod remains detachably connected to the slidable stud since these two components remain in sliding contact with the inner surface of the lumen of the outer catheter member. Once the outer catheter is retracted from the mating junction of the actuator rod and slidable stud, the mating portions of these components are no longer held in place and the actuator rod can be detached from the slidable stud. Likewise, a retractable outer sheath can extend over the outer catheter member to maintain the integrity of the mating junction between the mounting body and outer catheter member. Once the retractable outer sheath is retracted, the mating junction becomes uncovered allowing the outer catheter member to detach from the mounting body. Accordingly, the delivery system provides a mechanism for placing the fixation device into the desired body location and allows manipulation of the actuating mechanism to move the gripping elements into the desired locked position. The detachable coupling components associated with the delivery system allows the fixation to be implanted at the desired location and later detached from the delivery system once the fixation device is to permanently locked in place.

The delivery device of the invention is adapted to allow the user to deliver the fixation device to the target site from a remote access point, whether through endovascular or surgical approaches, align the device with the target tissue, and to selectively close, open, invert, lock or unlock the distal element. In some embodiments, the delivery catheter will have a highly flexible, kink resistant, torsionally stiff shaft with minimal elongation and high compressive strength.

The delivery system used to advance the fixation device into the desired location relies on an additional interventional system (not part of the present invention) can be used to position a guide catheter from outside of the patent into the target location (usually the heart). The system includes a guide wire which is advanced near the location where the fixation devices are to be implanted. A dilating catheter is advanced over the guide wire to create a transseptal puncture into the heart. Once the transseptal puncture has been made, the distal end of a guide catheter is advanced over the dilating catheter and introduced into the heart chamber. The dilating catheter and guide wire are then removed leaving only the guide catheter in place. The inner lumen of the guide catheter provides a sufficient sized lumen for advancing the delivery catheter carrying the fixation device into the heart chamber for implantation. The guide catheter should have a size, material, flexibility and other characteristics suitable for the application in which it is being used. For mitral valve repair, the guide catheter can be configured to be introduced in a femoral vein and advanced through the inferior vena cava into the heart, across a penetration in the interatrial septum, and into alignment with the mitral valve in the left atrium. Alternatively, the guide catheter can be configured for introduction in a femoral, axillary, or brachiocephalic artery and advancement through the aorta and aortic valve into the ventricle where it is steered into alignment with the mitral valve. In a further alternative procedure, the guide catheter may be configured for introduction through a puncture or incision in the chest wall and through an incision in the wall of the heart to approach the mitral valve or tricuspid valve.

In an exemplary method of use, the tissue site comprises first and second leaflets, and the step of moving the distal elements comprises coapting the leaflets. The leaflets may be part of a variety of tissue structures, but are preferably part of a cardiac valve such as the mitral valve. One preferred method of the present invention comprises inserting into the heart via transcatheter delivery a first fixation device and attaching the first fixation device to a first leaflet of the heart valve. This method includes inserting into the heart via transcatheter delivery a second fixation device and attaching the second fixation device to a second leaflet of the heart valve. The first fixation device is coupled to the second fixation device. Another preferred method includes positioning the first fixation device relative to the send fixation device to position the first leaflet relative to the second leaflet. The method may include locking the position of the first fixation device relative to the second fixation device. In another preferred method, a coupling system is used to couple and position the first fixation device relative to the second fixation device.

In another exemplary embodiment, the tissue site comprises first, second and third leaflets, and the step of moving the distal elements comprises coapting the leaflets. The leaflets may be part of a variety of tissue structures, but are preferably part of a cardiac valve such as the tricuspid valve. One preferred method of the present invention comprises inserting into the heart via transcatheter delivery a first fixation device and attaching the first fixation device to a first leaflet of the heart valve. This method includes inserting into the heart via transcatheter delivery a second fixation device and attaching the second fixation device to a second leaflet of the heart valve. A third fixation device is inserted into the heart via transcatheter delivery and attach to the third leaflet of the heart valve. The first, second and third fixation devices are coupled together. Another preferred method includes positioning the first, second and third fixation devices relative to each other to position the first, second and third leaflets relative to each other. Further, the method may include locking the position of the first, second and third fixation devices relative to each other. In another preferred method, a coupling system is used to couple and position the three fixation devices relative to each other.

These and other advantages of the invention will become apparent when the specification is read in conjunction with the drawings and the detailed description of some embodiments.

BRIEF DESCRIPTION OF THE DRAWINGS

FIG. 9A is a schematic view depicting a first fixation device being attached to a first tissue (leaflet of a mitral valve) within a patient.

FIG. 9D is a schematic view depicting the end of the retraction sheath adjacent to the first and second fixation devices allowing the coupling system to draw and position the fixation devices in close proximity of each other.

FIG. 9E is a schematic view showing the retraction sheath and shaft of the coupling wire removed from the patient leaving only the first fixation device and second fixation coupled and positioned in close proximity to each other within the patient.

FIG. 10A is a schematic view depicting a first fixation device with a coupling wire being attached to a first tissue (leaflet of a mitral valve) within a patient.

FIG. 10B is a schematic view depicting a second fixation device being attached to a second tissue (leaflet of a mitral valve) within a patient.

FIG. 10C is a schematic view depicting a retraction sheath and the shaft of the coupling wire with the end of the retraction sheath in close proximity to the second fixation device within the patient.

FIG. 10D is a schematic view showing the retraction sheath and the shaft of the coupling wire removed from the patient leaving only the first fixation device and second fixation coupled and in positioned in close proximity to each other within the patient.

FIG. 11A is a plan view depicting an embodiment of a coupling system for attaching fixations devices together.

FIG. 11B is a side cross-sectional view of the device shown in FIG. 11A.

FIG. 11C is a detail of FIG. 11B identified by the circle marked "11C."

DETAILED DESCRIPTION OF THE PREFERRED EMBODIMENTS

I. Cardiac Physiology

The human heart has four chambers, namely, the left atrium, the left ventricle, the right atrium and the right ventricle. The right atrium and the right ventricle together are sometimes referred to as the right heart. Similarly, the left atrium and the left ventricle together are sometimes referred to as the left heart. The left side of the heart provides the pumping action which supplies oxygenated blood to the arteries. The right side of the heart receives spent blood from the veins and pumps such blood to the lungs for oxygenation. The left atrium receives the oxygenated blood from the lungs via one of the four pulmonary veins. Blood from the left atrium is initially pumped into the chamber of the left ventricle which then pumps blood to the arteries. The left atrium is connected to the left ventricle by the mitral valve which is configured as a "check valve" which prevents back flow when pressure in the left ventricle is higher than that in the left atrium.

Figure 1:
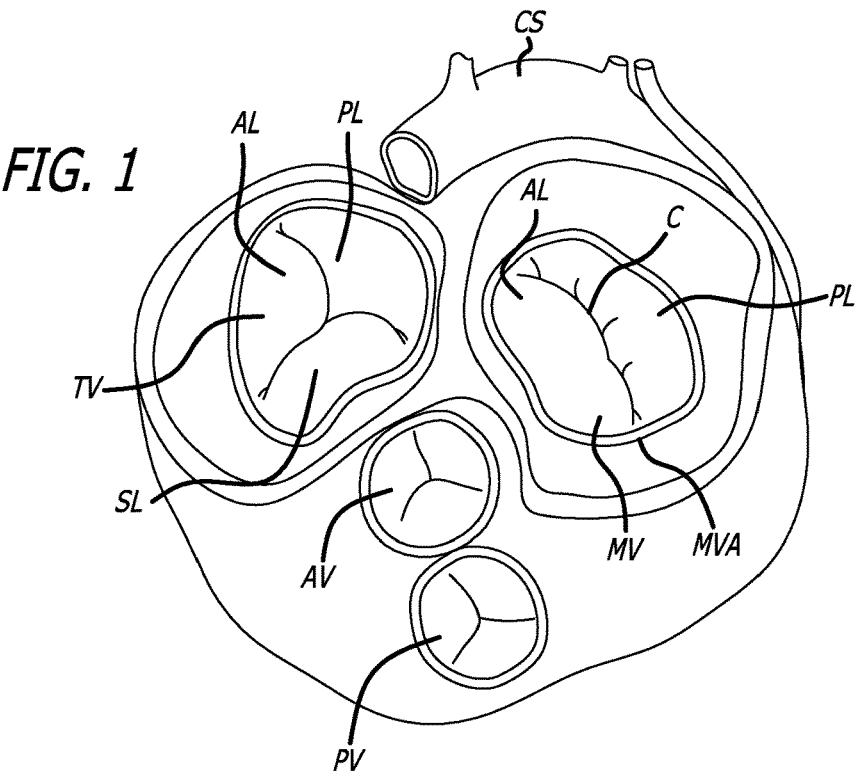
FIG. 1 is a cross-sectional view taken across the right and left atrium of a normal human heart in systole showing the four (4) valves of the heart and illustrating the free edges of the leaflets in normal coaptation.

A cross-sectional view of a normal human heart in systole is illustrated in FIG. 1. The cross section is taken across the right and left atrium so as to show the four (4) valves of the heart. During the normal heart cycle, the left ventricle, being the main pumping chamber of the heart, contracts causing the accumulated blood within this chamber to flow outwardly through the tricuspid (aortic) valve AV into the aorta which then is distributed to many arteries of the patient. Back flow of blood or "regurgitation" through the mitral valve MV back into the left atrium as the left ventricle contracts is prevented since the mitral valve MV, acting as a "check valve," closes to prevent back flow when pressure in the left ventricle is higher than that in the left atrium. The mitral valve MV comprises a pair of leaflets, namely, the posterior leaflet PL and anterior leaflet AL, having free edges which meet evenly to close, as illustrated in FIG. 1. The opposite ends of the leaflets are attached to the surrounding heart structure along an annular region referred to as the annulus. The free edges of the leaflets are secured to the lower portions of the left ventricle through chordae tendinae (referred to hereinafter as the chordae) which include plurality of branching tendons secured over the lower surfaces of each of the valve leaflets. The chordae, in turn, are attached to the papillary muscles which extend upwardly from the lower portions of the left ventricle and intraventricular septum. The aortic valve AV and pulmonary valve PV are the other two valves of the human heart. FIG. 1 shows the location of the coronary sinus CS and mitral valve annulus MVA in relationship to the four valves of the heart.

Figure 2:
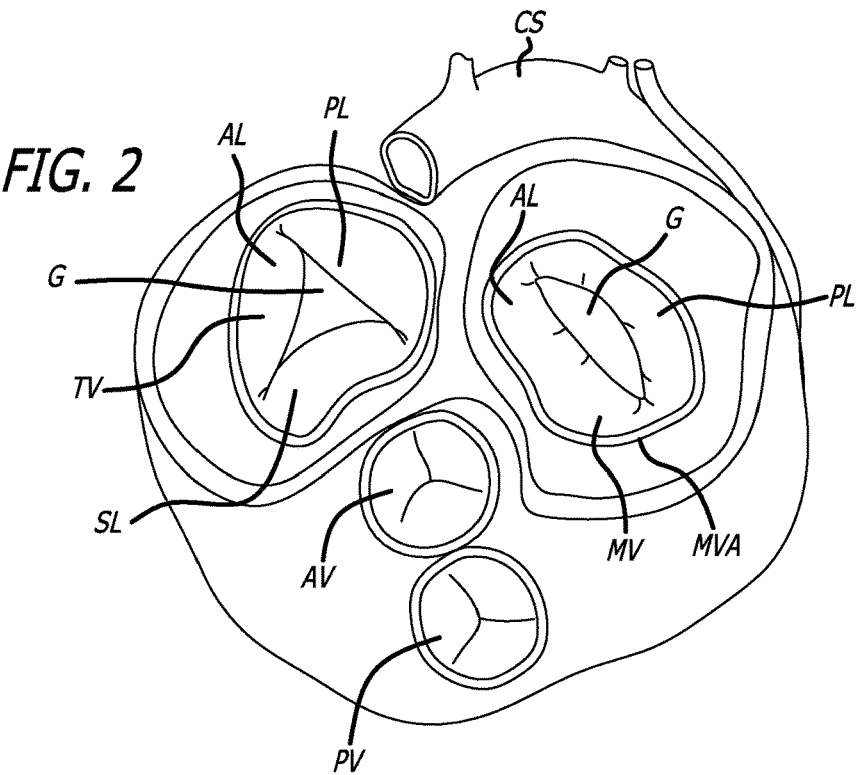
FIG. 2 is a cross-sectional view taken across the right and left atrium of a normal human heart in systole showing the four (4) valves of the heart and illustrating the free edges of the leaflets of the mitral valve and tricuspid valve in regurgitative coaptation.

A number of structural defects in the heart can cause mitral valve regurgitation. Regurgitation occurs when the valve leaflets do not close properly allowing leakage from the ventricle into the atrium. As shown in FIG. 1, the free edges of the anterior leaflet AL and posterior leaflet PL normally meet along a line of coaptation C. An example of a defect causing regurgitation is shown in FIG. 2. Here an enlargement of the heart causes the mitral annulus to become enlarged, making it impossible for the free edges of the anterior leaflet AL and posterior leaflet PL to meet during systole. This results in a gap G which allows blood to leak through the mitral valve MV during ventricular systole. Ruptured or elongated chordae can also cause a valve leaflet to prolapse since inadequate tension is transmitted to the leaflet via the chordae. While the other leaflet maintains a normal profile, the other leaflet does not which creates a gap between the two valve leaflets and causes leakage from the left ventricle back into the left atrium. Such regurgitation can also occur in patients who have suffered ischemic heart disease where the left ventricle does not contract sufficiently to effect proper closure.

The right heart consists of two chambers, the right atrium and the right ventricle, separated by a valve, the tricuspid valve TV. The right atrium receives blood almost continuously from the body's two major veins, the superior and inferior venae cavae. The right ventricle tapers into the pulmonary trunk, into which it ejects blood when contracting. The pulmonary trunk branches into the left and right pulmonary arteries that carry the blood to each lung to be oxygenated. The tricuspid valve TV prevents back flow of blood from the right ventricle into the right atrium during ventricular systole when it closes and allows blood to flow from right atrium into right ventricle during ventricular diastole when it opens. Blood flows from the right ventricle through the pulmonary valve to the lungs where the blood will be oxygenated. This tricuspid valve TV can be weakened, for example, by drug abuse, endocarditis, rheumatic fever, heart disease and congenital abnormality. The back flow of blood is also known as tricuspid insufficiency or tricuspid regurgitation. As with the mitral valve, the three leaflets of the tricuspid valve, namely, the anterior leaflet AL, posterior leaflet PL, and the septal leaflet SP, normally converge in a normal fashion at a common point of meeting near the center of the tricuspid valve TV, as is shown in FIG. 1. When damaged, these leaflets no longer close tightly to prevent backflow of blood into the right atrium as the right ventricle contacts. An example of a defect causing tricuspid regurgitation is shown in FIG. 2. As a result of the free ends of the leaflets no longer meeting, undesired tricuspid regurgitation occurs. This results in a gap G which allows some blood to leak through the tricuspid valve TV back into the right atrium during ventricular systole.

II. General Overview

Figure 3:
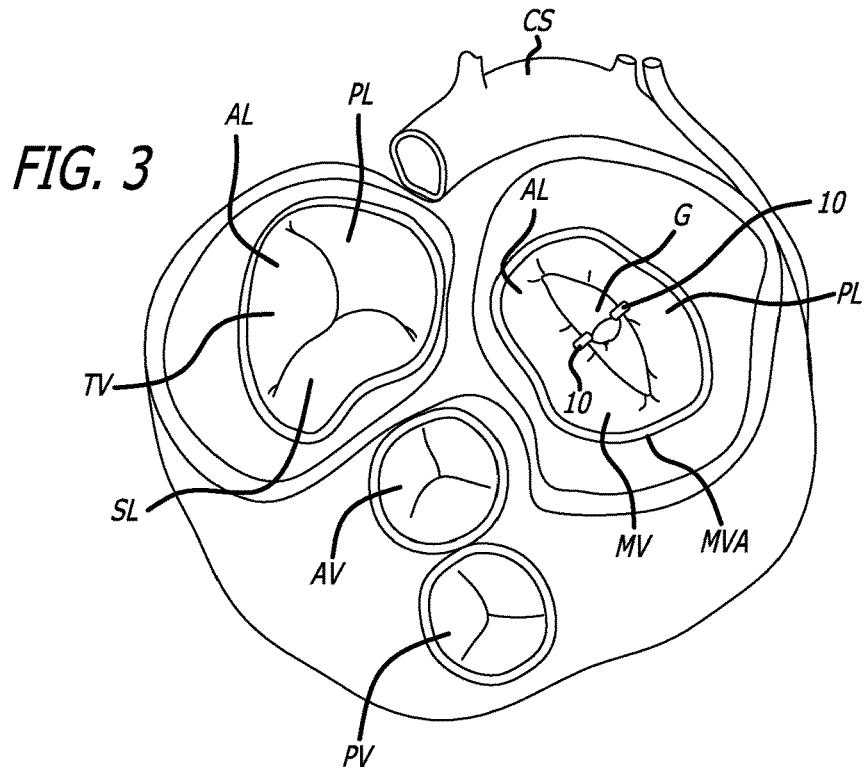
FIG. 3 is a cross-sectional view of the heart depicted in FIGS. 1 and 2 in which fixation devices made in accordance with the present invention are placed on the leaflets of the mitral valve, namely, the anterior leaflet and posterior leaflet.
Figure 4:
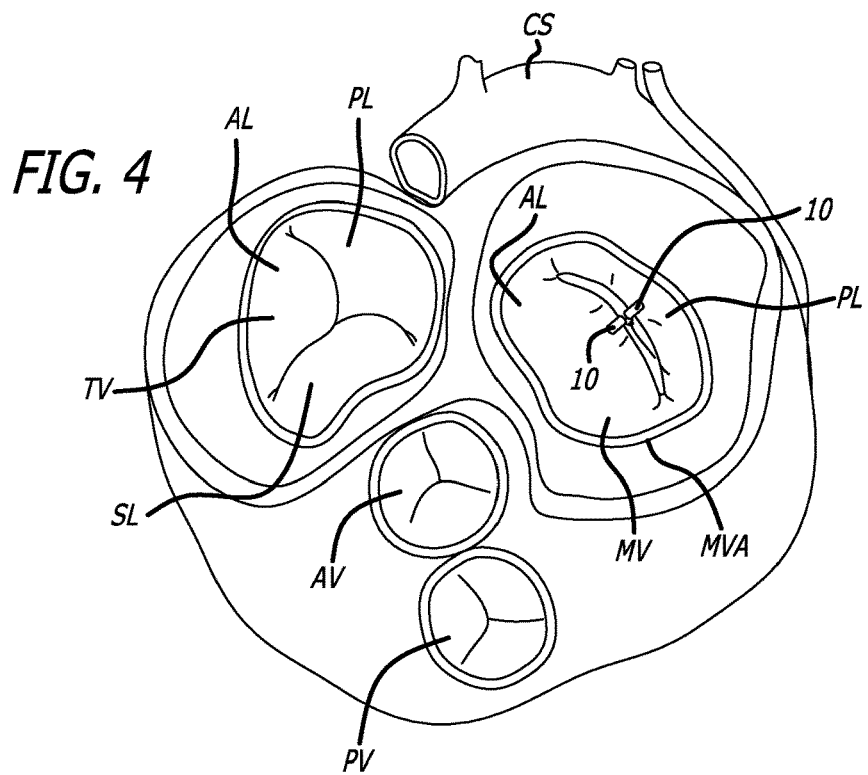
FIG. 4 is a cross-sectional view of the heart depicted in FIG. 3 with the fixation devices coupled and positioned in close proximity to each other to cause the anterior leaflet and posterior leaflet of the mitral valve to be drawn in close proximity to each other.

The present invention provides methods, systems and devices for grasping, positioning and fixating tissues, such as valve leaflets, to treat cardiac valve regurgitation, particularly mitral valve and tricuspid regurgitation. As a consequence of connecting and positioning damaged valve leaflets closer together, the particular valve will close more completely during the systole and therefore more effectively fulfill a function of a one way fluid valve which helps to prevent regurgitation. The placement of fixation devices 10 shown in FIGS. 3 and 4 on the anterior leaflet AL and posterior leaflet PV of the mitral valve MV allows the gap G formed during ventricular systole to be reduced to help reduce the effects of regurgitation. Initially, a fixation device is placed on each of the anterior leaflet AL and posterior leaflet PL as is shown inn FIG. 3. Since the two fixation devices 10 are coupled to each other, it is possible to move the fixation devices 10 is closer proximity to each other as is shown in FIG. 4. As a result, the free ends of the anterior leaflet AL and posterior leaflet PL are also re-positioned and remain in close proximity to each other resulting in a reduction of the gap formed between the leaflets.

Figure 12:
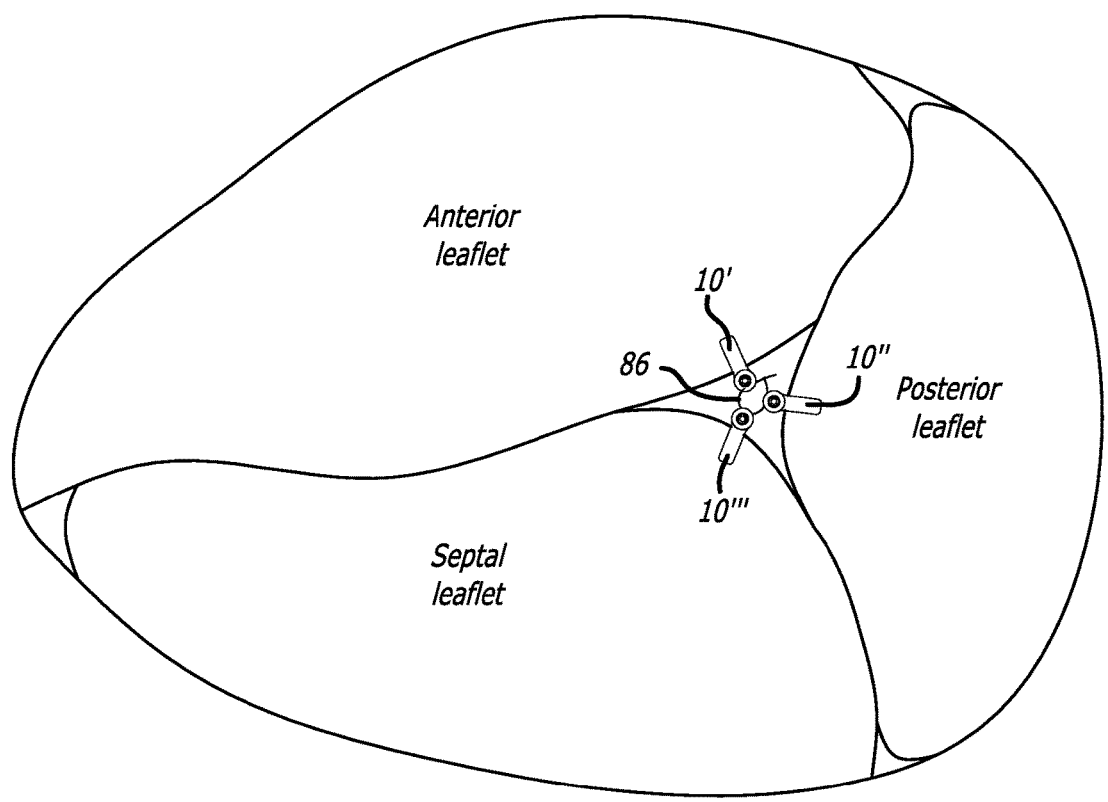
FIG. 12 is a schematic plan view of a tricuspid valve of a human heart, showing fixation devices made in accordance with the present invention placed on the three leaflets of the tricuspid valve, namely, the anterior leaflet, posterior leaflet, and the septal leaflet, which allow these leaflets to converge in a normal fashion at a common point of meeting near the center of the valve.

Additionally, the invention is suitable for repairing the tricuspid valve in the heart of a patient via a transcatheter procedure. A gap G, as is shown in FIG. 2, can be formed when the free ends of the three leaflets of a damaged tricuspid valve do not meet at the common central point. Referring now to FIG. 12, three fixation devices 10', 10" and 10''' are shown attached to each of the free ends of all three of the leaflets of the tricuspid valve to help reduce tricuspid regurgitation. An objective of the system of the present invention is to provide a mechanism that securely grips the common points of all three of the leaflets of a tricuspid valve at a central point to reduce the size of the gap G which may have been formed due to damage upon the tricuspid valve. As a consequence of this connection, the three leaflets of the tricuspid valve close more completely during the systole and therefore more effectively fulfill a function of a one-way valve which helps to prevent tricuspid regurgitation.

Grasping of the target tissue of the fixation device 10 will preferably be atraumatic which provides a number of benefits. By atraumatic, it is meant that the devices and methods of the invention may be applied to the valve leaflets and then removed without causing any significant clinical impairment of leaflet structure or function. The leaflets and valve continue to function substantially the same as before the invention was applied. Thus, some minor penetration or denting of the leaflets may occur using the invention while still meeting the definition of "atraumatic." This enables the devices of the invention to be applied to a diseased valve and, if desired, removed or repositioned without having negatively affected valve function. In addition, it will be understood that in some cases it may be necessary or desirable to pierce or otherwise permanently affect the leaflets during either grasping, fixing or both. A general overview of the basic features will be presented herein. Such features are not intended to limit the scope of the invention and are presented with the aim of providing a basis for descriptions of individual embodiments presented later in the application.

III. Fixation Devices and Delivery Systems

When describing the devices of the invention herein, "proximal" shall mean the direction toward the end of the device to be manipulated by the user outside the patient's body, and "distal" shall mean the direction toward the working end of the device that is positioned at the treatment site and away from the user.

Figure 5:
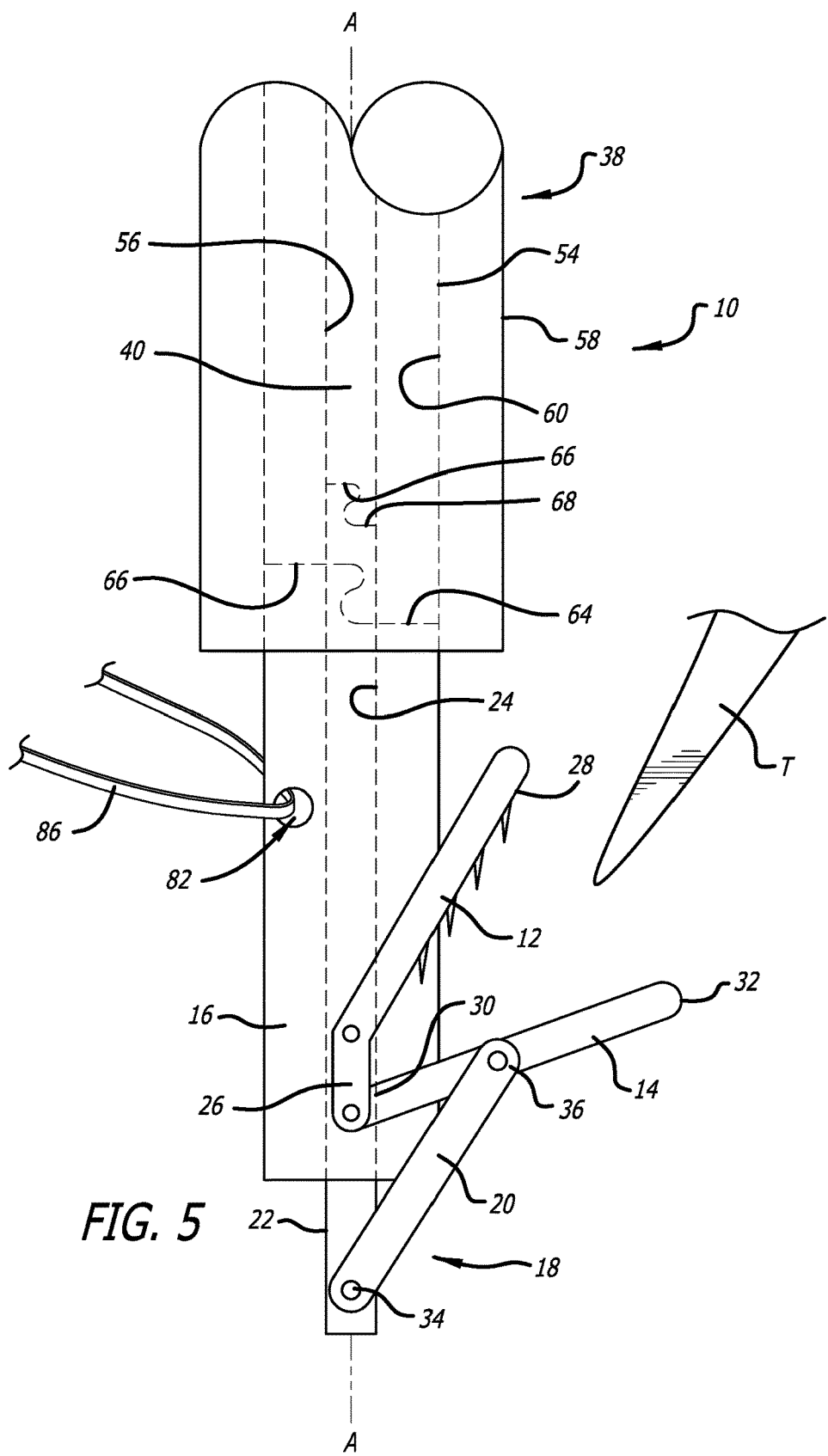
FIG. 5 is a side view of a particular embodiment of fixation device and a particular embodiment of a delivery system made in accordance with the present invention system, as shown in FIGS. 3 and 4, with the fixation device depicted in a first, open condition.

Referring now to FIGS. 5-8, a fixation device 10 and delivery system for delivering and implanting the fixation device 10 are illustrated. The fixation device 10 includes a first gripping element 12 and a second gripping element 14 which are mounted on a mounting body 16. One or both of these gripping elements 12,14 can be movable to allow the gripping elements 12, 14 to move between a first open position, as is shown in FIG. 5, and a second closed position, as is shown in FIG. 6A. The gripping elements 12, 14 are also movable and lockable in multiple positions between the first open position and the second closed position. The gripping elements protrude radially outward and are positionable on opposite sides of the target tissue T as shown so as to capture or retain the tissue T therebetween. The target tissue T is usually the free end of a leaflet of a heart valve.

As can be seen in FIG. 5, the gripping elements 12, 14 are in the first open position to allow the interventionalist to position the gripping elements 12, 14 to engage and capture the tissue T between these elements. The fixation device 10 includes an actuating mechanism 18 designed to move one or both of the gripping elements 12, 14 between the open and closed positions. As can be seen in FIG. 5, the actuating mechanism includes a link 20 which is pivotally mounted to a slideable stud 22 which extends within a lumen 24 extending through the mounting body 16. The movement of the stud 22 causes the link 20 to pivot which, in turn, pivots the second gripping element 14. While a single link 20 is shown in the drawings, it should be appreciated that a second link (not shown) could be placed on the opposite side of the stud 22 to cooperate with the first link 20 in moving the second gripping element 14.

As can be seen in FIG. 5, the first gripping element 12 has a first end 26 pivotally mounted to the mounting body 16 and a free end 28 which extends radially away from the mounting body 16. Likewise, the second gripping element 14 has a first end 30 which is pivotally mounted to the mounting body 16, along with a movable, free end 32 which extends radially away from the mounting body 16. One end 34 of the link 20 is pivotally attached to the slidable stud 22 and the other end 36 is pivotally attached to the second gripping element 14. When the slidable stud 22 is moved longitudinally within the lumen of the mounting body 16, the link 20 imparts a force on the second gripping element 14 which moves the element 14 relative to the first gripping element 12. The direction of movement of the stud 22 will either move the second gripping element 14 towards or away from the first gripping element 12. In this manner, the interventionalist will be able to move the gripping elements 12, 14 into the proper open and closed positions by simply moving the stud 22 in a longitudinal direction.

Figure 6A:
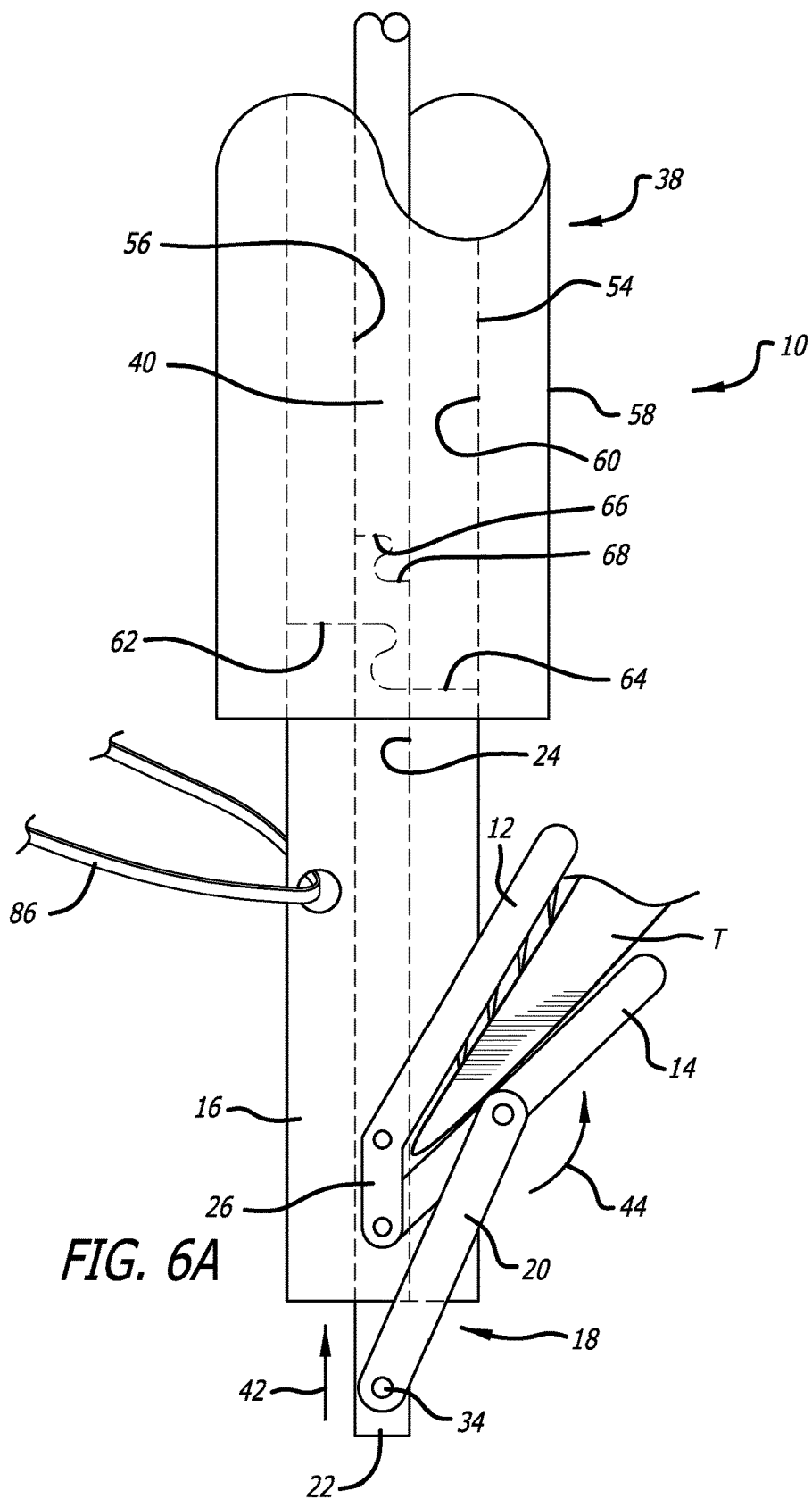
FIG. 6A is a side view of the fixation device of FIG. 5 in a second, closed condition in which the fixation device grasps a portion of targeted tissue.
Figure 6B:
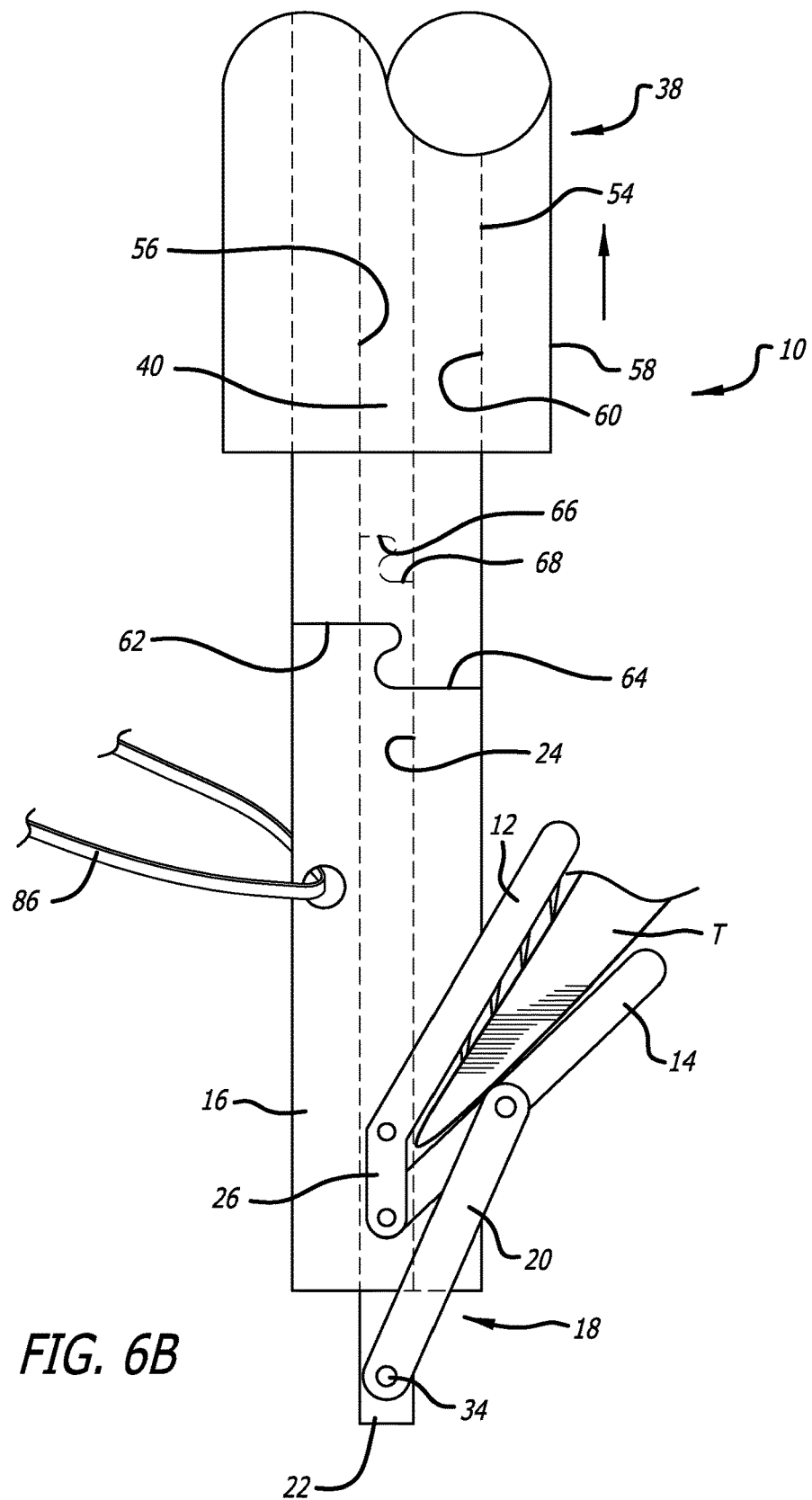
FIG. 6B is a detail view of the fixation device of FIG. 6A showing the restraining sheath of the delivery system being retracted.

The fixation device 10 is designed to be detached from a delivery catheter 38 to allow the fixation device to be permanently implanted in the patient. The delivery catheter 38 is also adapted to allow the interventionalist to attain the proper locking position for the gripping elements 12, 14. As can be seen in FIGS. 5-6B, the stud 22 is detachably connected to an actuating rod 40 which forms a portion of the delivery catheter 38. This actuator rod 40 has a proximal end (located outside of the patent) which is manipulated by the interventionalist to actuate the mechanism 18 to open and close the gripping elements 12, 14 in order to grasp the target tissue T. An arrow 42 in FIG. 6A shows the stud 22 being moved proximally to cause the link 20 to pivot the second gripping arm 14 (see arrow 44) into a closed position in which the tissue T is firmly gripped between the gripping elements 12, 14. The actuating mechanism 18 shown in the drawings illustrate a simple way to move the gripping elements 12, 14 into the various positions which can be attained. It should be appreciated that other ways in forming a suitable actuating mechanism can be utilized without departing from the spirit and scope of the invention.

Figure 8:
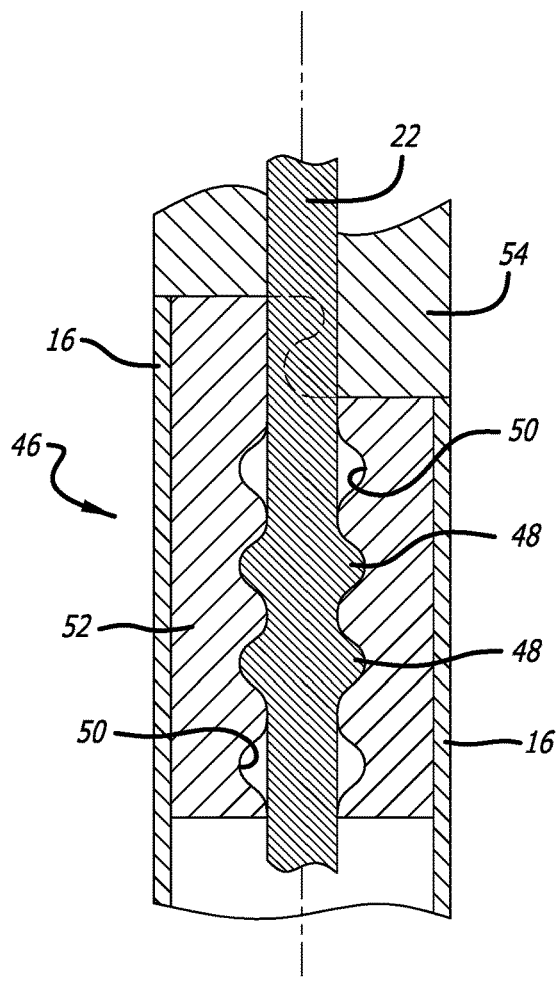
FIG. 8 is a side, cross-sectional view of a locking component associated with the fixation device disclosed in FIGS. 5-7A for locking the fixation device onto the tissue.

The fixation device 10 includes a locking mechanism 46 incorporated into the mounting body 16 and stud 22 for locking the griping elements 12, 14 in place after the tissue T has been grasped between the elements. One embodiment of a locking mechanism 46 is shown in FIG. 8 which illustrates a number of outward extending projections 48 formed on the slidable stud 22 which are designed to fit into specially sized and shaped recesses 50 associated with the mounting body 16.

In use, the slidable stud 22 is moved longitudinally within the lumen of the mounting body 16 in order to place the gripping elements 12, 14 in the proper locking position to achieve the necessary gripping force on the target tissue T. These outwardly extending projections 48 are disposed along a length of the stud 22 so as to create a somewhat frictional fit within the various recesses 50 formed on the mounting body 16. As can be seen in FIG. 8, the recesses 50 can be formed on a resilient component 52 which is also located within the lumen 24 of the mounting body 16. The resilient component 52 can be made from a number of plastic materials, or similar materials, which provide some "give" when the projections 48 are sliding in the areas between recesses 50. The recesses 50 are sized and shaped so as to engage with the projections 48 once a projection 48 is placed within a particular recess 50. This locking system will prevent the stud 22 from moving relative to the mounting body 16 until a sufficient amount of force is placed on the stud 16 (via movement of the actuator rod 40) to move the projections 48 out of their respective recesses and into adjacent recesses. Once the gripping elements 12, 14 have been placed in their proper locking position, the actuator rod 38 can be removed from the stud 22 (explained in greater detail below), allowing the fixation device 10 to remain implanted in the patient. The locking system should maintain the projections 48 on the stud 22 fully engaged within the recesses 50 thus preventing the gripping elements 12, 14 from moving out of their locked position.

The fixation device 10 is attached to additional components which form the delivery system 40. As can be seen in FIGS. 5-6B, the mounting body 16 is coupled to an outer catheter member 54 which, like the actuator rod 40, extends proximally outside of the patient to allow the catheter member 54 to be manipulated by the interventionalist. The outer catheter member 54 includes a lumen 56 in which the actuator rod 40 extends. The actuator rod 40 is slidable within this lumen 56 so that the rod 40 can be moved at its proximal end (not shown) by the interventionalist in order to lock the gripping elements 12, 14 on the target tissue T. Further, an outer sheath 58 extends over this outer catheter member 54. This outer sheath 58 includes a lumen 60 in which the outer catheter member 56 extends. This sheath 58 can be retracted by the interventionalist once the fixation device 10 has been implanted at the target site to disengage the member 54 and actuator rod 40 (as explained below) leaving only the fixation device implanted in the patient.

Figure 7A:
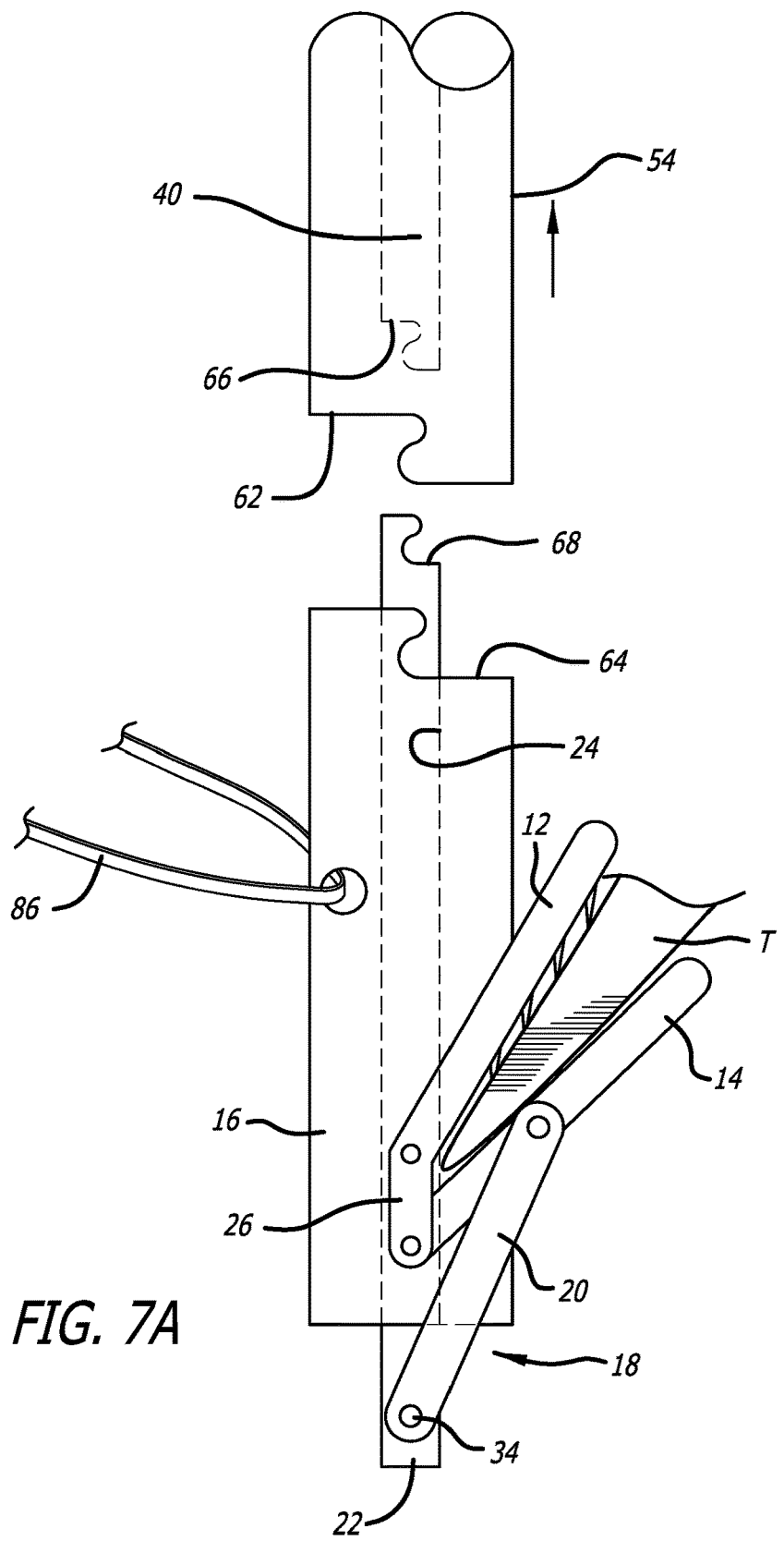
FIG. 7A is a detail view of the fixation device of FIG. 6B in which the actuator rod and outer catheter member of the delivery system have been released from the fixation device.
Figure 7B:
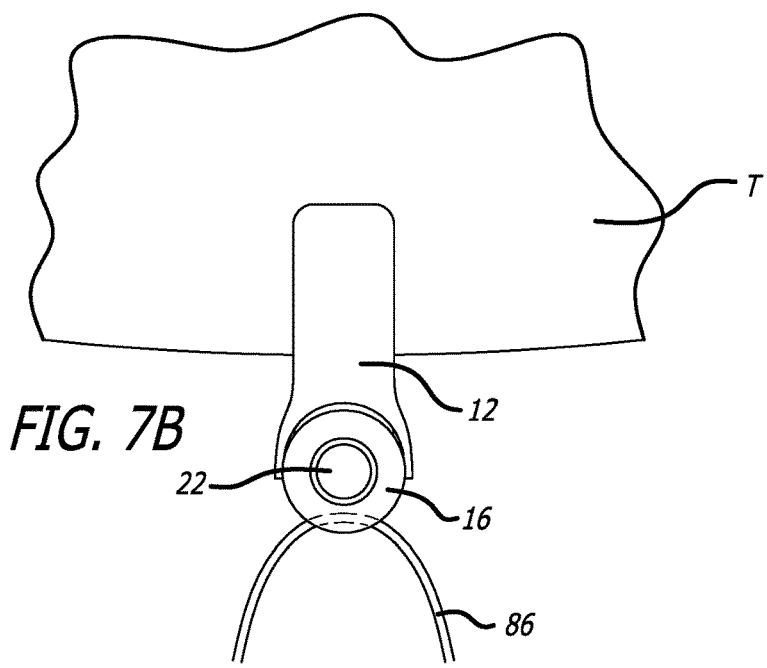
FIG. 7B is a plan view of the fixation device shown in FIGS. 5-7A grasping a portion of tissue.

In this regard, the outer catheter member 54 includes a mating junction 62 which engages a complementing mating junction 64 formed on the mounting body 16 of the fixation device 10. Similarly, the actuator rod 40 includes a mating junction 66 with the stud 22 including a complementary junction 66. These mating junctions allow the fixation device 10 to be detached from the delivery catheter 38 to allow the fixation device 10 to remain implanted in the patient. These mating junctions may have any shape or curvature which will allow or facilitate interlocking and later detachment. In use, the outer sheath 58 remains fixed over the mating junctions 62 and 64 formed on the outer catheter member 54 and mounting body 16 until it is desired to detach the delivery catheter 38 from the fixation device 10. The outer catheter member 54, in turn, remains disposed over the matting junctions 66, 68 of the actuator rod 40 and stud 22. The matting junctions 62-68 thus remain locked together until the component disposed over the particular junctions are retracted. As can be seen in FIG. 7A, the outer sheath 58 has been removed from its position over the mating junctions 62, 64 to allow the outer catheter member 54 to become detached from the mounting body 16. Likewise, the matting junctions 66, 68 of the actuator rod 40 and stud 22 are no longer covered by the outer catheter member 54 which allows these components to become detached from each other as well. Accordingly, these mating junctions allow the fixation device 10 to be detached from the delivery catheter 38 and be left behind as an implant to hold the target tissue T together in a coapted position.

The gripping elements 12, 14 of the fixation device 10 are preferably comprised of cobalt chromium, nitinol or stainless steel, however any suitable materials may be used. In most applications, such as the repair of the mitral valve, the fixation devices are designed to be permanently implanted in the patient. In such applications, it is often desirable to promote tissue growth around the fixation device 10. For this purpose, some or all of the components of the fixation device can be preferably covered with a covering or coating (not shown in the drawings) to promote tissue growth. In one embodiment, a biocompatible fabric cover (not shown) can be positioned over the gripping elements 12, 14 and mounting body 16. The cover may optionally be impregnated or coated with various therapeutic agents, including tissue growth promoters, antibiotics, anti-clotting, blood thinning, and other agents. Alternatively or in addition, some or all of the fixation element and/or covering may be comprised of a bioerodable, biodegradable or bioabsorbable material so that it may degrade or be absorbed by the body after the repaired tissues have grown together.

A device/system for coupling and locking two or more fixation devices is shown in FIGS. 9A-11. Each fixation device 10 used to reposition the target tissue has associated with it a coupling device/system that is adapted to couple separate fixation devices together and to move these same fixation devices relative to each other once the devices are attached to the target tissue. In one particular embodiment, the coupling device/system includes a coupling wire 80 designed to be attached to the fixation device 10 utilizing attachment structure, for example, openings or receiving ports 82 formed on the fixation device 10 to receive the wire 80 therethrough. FIGS. 5-7B show one embodiment of such a port 82 that can be formed on each fixation device. FIGS. 9A-10D show different schematic representations depicting suitable methods (described in greater detail below) for implanting and maneuvering fixation devices in order to reduce the size of any gap formed between the leaflets of a damaged heart valve.

The distal end 84 of the coupling wire 80 is shown in FIGS. 11A-11C which creates a coupling component for maintaining the devices coupled together once implanted at the target site. The distal end 84 includes a very thin coupling device 86, similar to a zip tie wire, which is formed from an insoluble polymer. This coupling device 86 is threaded through the openings or ports 82 formed on the fixation devices and is detachable from the remainder of the coupling wire 80 so as to remain implanted in vivo with the implanted fixation devices. As in the case of a typical zip tie that is known in the art, the coupling wire has a proximal end 88 which is placed into the port 82 formed on the fixation device. The coupling device 86 has a lock 90 at an opposite end of the wire 80. Zip ties (also known as Cable Ties) are well known in the art, as exemplified by U.S. Pat. No. 5,956,813 and the art cited therein which are incorporated herein by reference. The free end 88 is threaded through the lock 90 so that when the free end is pulled in one direction through the lock, the distal coupling device 86 cannot be pulled back in the other direction due to ratcheting means molded into the lock 90 and the length of the coupling device 86. A weakened frangible coupling 92 is located at the junction between the end of the coupling device 86 and the proximal portion of the coupling wire 80 so that a sharp tug on the coupling wire 80 will break the coupling 92 at the frangible portion detaching the coupling device 86 from the remainder of the coupling wire 80. In this regard, see, FIGS. 11A-11C, where a frangible coupling 92 is exemplified. In this embodiment, the frangible coupling 92 includes a length having reduced thickness in relation to the thickness in the vicinity of the frangible zone. This reduced thickness gives rise to the result that, should the coupling device 86 be tensioned to a threshold amount of force, then the coupling component 86 will break at the frangible connection 92, and at no other place along the length of the wire 80. Thus, as will be explained below, the interventionalist is able to pull the coupling wire 80 which initially draws the fixation devices 10 in close proximity to each other. The target tissue is, in turn, drawn closer to each other to reduce the size of any gap formed therebetween. Once the interventionalist deems that the devices and tissue are properly positioned, the interventionalist can give the coupling wire 80 a sharp tug which allows the coupling device 86 to break away from the remainder of the coupling wire 80.

IV. Methods of Use

Deployment of each fixation device with its associated delivery catheter can be done in a number of different ways. Two such methods are disclosed herein in FIGS. 9A-9E and 10A-10D. In using the delivery system to advance the fixation device into the desired location, an additional interventional system (not part of the present invention) can be used to position a guide catheter from outside of the patent into the target location (usually the heart). The system includes a guide wire which is advanced near the target location where the fixation devices are to be implanted. A dilating catheter is advanced over the guide wire to create a transseptal puncture into the heart. Once the transseptal puncture has been made, the distal end of a guide catheter is advanced over the dilating catheter and introduced into the heart chamber, the dilating catheter and guide wire then being removed leaving only the guide catheter in place. The inner lumen of the guide catheter provides a sufficient sized lumen for advancing the delivery catheters carrying the fixation devices into the heart chamber for implantation. The guide catheter should have a size, material, flexibility and other characteristics suitable for the application in which it is being used. For mitral valve repair, the guide catheter can be configured to be introduced in a femoral vein and advanced through the inferior vena cava into the heart, across a penetration in the interatrial septum, and into alignment with the mitral valve in the left atrium. Alternatively, the guide catheter can be configured for introduction in a femoral, axillary, or brachiocephalic artery and advancement through the aorta and aortic valve into the ventricle where it is steered into alignment with the mitral valve. In a further alternative, the guide catheter may be configured for introduction through a puncture or incision in the chest wall and through an incision in the wall of the heart to approach the mitral valve.

The delivery catheter is placed into the left atrium of the heart of the patient according to known methodology until the distal end of the delivery catheter is positioned directly above the mitral valve. The distal end of the catheter is then advanced gently through the two leaflets of the mitral valve into the left ventricle. At this point, the gripping elements of the fixation device may be in a closed, collapsed position to facilitate a narrow delivery profile. The actuator rod can then be manipulated to place the gripping elements into the first open position to allow the target tissue to be positioned between the two gripping elements. Once the tissue has been properly positioned between the gripping elements, the actuator rod can be retracted causing the coupling mechanism associated with the fixation device to draw the gripping elements into their locked, gripping position. The interventionalist can then determine if the fixation device is properly grasping the target tissue at the desired location. If not, the interventionalist can manipulate the actuator rod to re-open the gripping elements to re-position the gripping elements on the tissue. After the fixation device is deemed in proper position, the delivery catheter can be disengaged.

Referring now to FIGS. 9A-9E, in a particular exemplary method of use, the tissue site comprises first and second leaflets, and the step of moving the distal elements comprises coapting the leaflets. The leaflets may be part of a variety of tissue structures, but are preferably part of a cardiac valve such as the mitral valve. FIGS. 9A-9E show the method in simplified, schematic drawings after a guide catheter (not shown) has been placed within the left atrium of the patient's heart. It should be appreciated that FIGS. 9A-9E are schematic representations of a basic method for performing a mitral valve procedure. For this reason, components are shown located outside the patient's body in these figures. In an actual procedure, these components would be placed within the lumen of the guide catheter which extends outside of the patient into the left atrium of the patient's heart.

Initially, a first fixation device 10' is inserted into the right atrium of the heart and is attached to a first target tissue, such as the anterior leaflet AL of the mitral valve, as is shown in FIG. 9A. This fixation device 10' would, of course, be delivered via its associated delivery catheter which is not shown in FIG. 9A. This fixation device 10' is shown attached to the coupling wire 80 used to couple the first fixation device 10' to a second fixation device 10". The second fixation device 10" remains outside of the patient in its delivery catheter (shown in FIG. 9A) as the first fixation device 10' is being attached to the anterior leaflet 10'. As can be seen in FIG. 9A, the second fixation device 10" is initially coupled to the coupling wire 80 outside of the patient so that when it is delivered and implanted to the posterior leaflet, the coupling wire 80 will already be in coupling engagement with these two fixation device 10', 10". The coupling wire 80 is shown extending through the port 82 formed on each fixation device 10', 10".

Figure 9B:
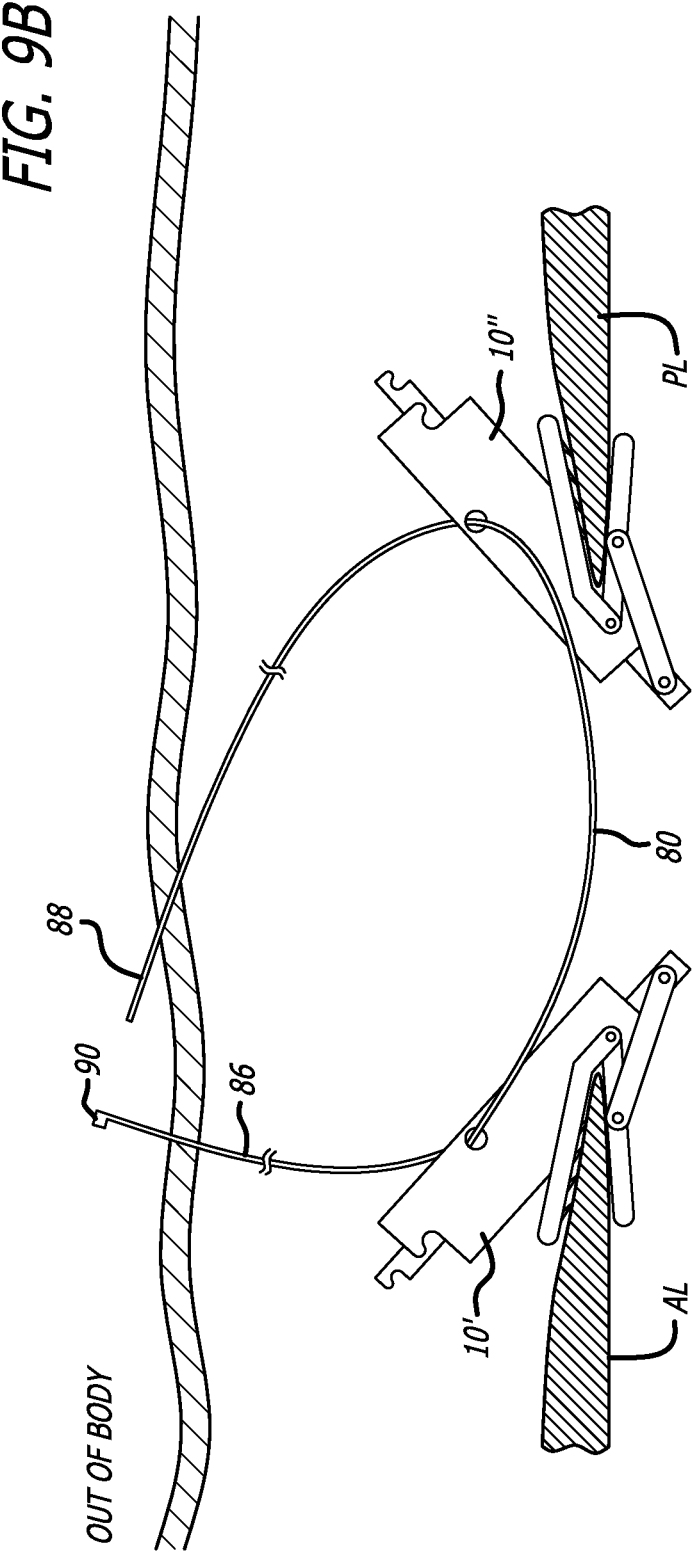
FIG. 9B is a schematic view depicting a second first fixation device being attached to a second tissue (leaflet of a mitral valve) within a patient.
Figure 9C:
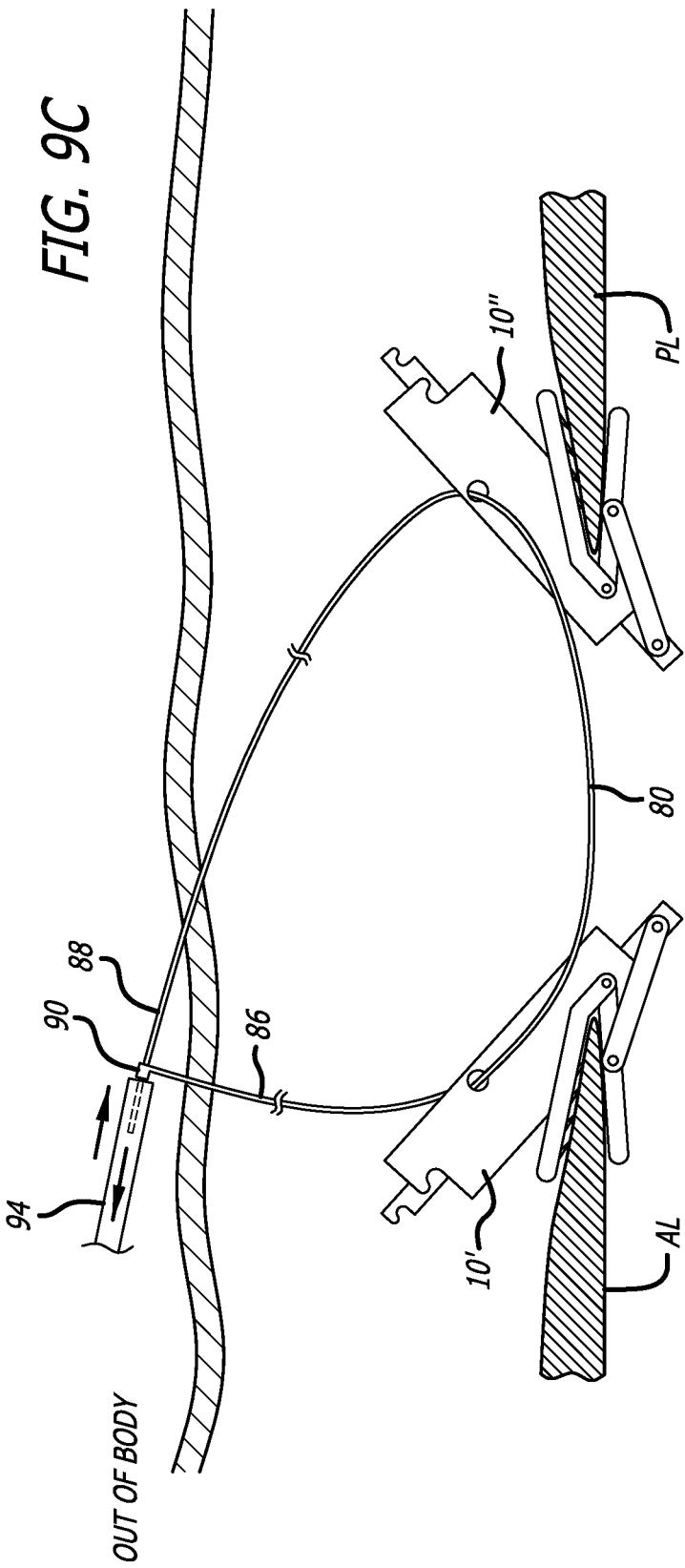
FIG. 9C is a schematic view depicting a retraction sheath which is to be advanced to the general location of the first fixation device and second fixation device implanted within a patient.

FIG. 9B shows the second fixation device 10" affixed to the second target tissue, namely, the posterior leaflet PL of the mitral valve. The coupling wire 80 can be actuated to allow the distal end of the wire 80, which includes the locking device 86, to couple and lock these two fixation devices 10', 10" in close proximity to each other. Referring now to FIG. 9C, the end of the coupling wire 80 is placed into the lock 90 of the coupling component 86. A sliding catheter 94 can then be used to position the lock 90 of the coupling component 86, located at the distal end of the coupling wire 80, towards the implanted devices 10', 10." Referring now to FIG. 9D, the sliding catheter 94 is shown positioned close to the implanted fixation devices 10', 10". The proximal end of the coupling wire 80 (located outside of the patient) can now be retracted proximally to cause the loop of the coupling component 86 to tighten or to be drawn to a smaller diameter which, in turn, causes the fixation devices 10', 10" to move in close proximity to each other. Accordingly, the free ends of the anterior leaflet AL and posterior leaflet PL will move, in turn, in close proximity to each other in order to close the gap formed between these leaflets. Finally, the interventionalist applies a tug (as distinguished from a gentle pull) on the proximal end of the coupling wire 80 which causes the frangible coupling 92 of the wire 80 to break at the point of its connection to the coupling component 86. The coupling wire 80 and sliding catheter 94 can then be removed leaving only the two fixation devices 10', 10" and the coupling component 86 left implanted within the patent as is shown in FIG. 9E.

FIGS. 10A-10D shows another alternative method for coupling the fixation devices 10', 10" together. As can be seen in FIG. 10A, the first fixation device 10' is attached to a first target tissue, such as the anterior leaflet AL of the mitral valve. As can be seen in FIG. 10A, one end of the coupling wire 80 is physically attached to the first fixation device 10' with the other end extending outside of the patient. A second fixation device 10" is connected to the coupling wire 80 via the coupling port 82 formed on the device. In this particular device 10", the port includes a lock 90 which acts to lock the coupling component 86 once the fixation device 10', 10" are affixed to the target tissue. As can be seen in FIG. 10B, the second fixation device 10" is advanced on the coupling wire 80 and placed on the free end of the posterior leaflet PL. A sliding catheter 94 can then be advanced along the coupling wire 80 to a location adjacent to the second fixation device 10" as is shown in FIG. 10C. The interventionalist can then proximally retract the coupling wire 80 to cause the first fixation device 10' to move in close proximity to the second fixation device 10" as is shown in FIG. 10D. Once the devices 10', 10" are properly positioned in the patient, the interventionalist can apply a firm tug (as distinguished from a gentle pull) on the proximal end of the coupling wire 80, which again causes the frangible coupling 92 of the wire 80 to break at the point of connection to the coupling component 86. The coupling wire 80 and sliding catheter 94 can then be removed leaving only the two fixation devices 10', 10" and the coupling component 86 left implanted within the patent.

In another exemplary method of using the fixation devices and systems of the present invention, the tissue site comprises first, second and third leaflets, and the step of moving and coupling the fixation devices comprises coapting the three leaflets. The leaflets may be part of a variety of tissue structures, but are preferably part of a cardiac valve such as the tricuspid valve, the aortic valve or the pulmonary valve. The method is similar to the method described above with respect to the mitral valve, except that a third fixation device 10''' is used to grasp the third leaflet of the valve. The first and second fixation devices 10', 10" are initially affixed to the anterior leaflet AL and posterior leaflet PL of the tricuspid valve utilizing their respective delivery catheters. The third fixation device 10''' is attached to the third target tissue, namely, the septal leaflet. The method includes coupling these three fixation devices and positioning them relative to each other by manipulating the coupling wire which couples each device together. These three fixation devices 10', 10" and 10''' are shown in FIG. 12 attached to their respective leaflets. The coupling wire 80 can be coupled to the fixation devices in a manner as is shown in FIGS. 9A-9E or one end of the coupling wire 80 could be attached to one of the fixation devices as is disclosed in the method depicted in FIGS. 10A-10D.

Accordingly, there is described a novel device, system and method that address needs in the art for capturing and connecting the free ends of the leaflets of the mitral valve or tricuspid heart valve. The present invention may, of course, be carried out in other specific ways than those herein set forth without departing from the essential characteristics of the invention. The present embodiments are, therefore, to be considered in all respects as illustrative and not restrictive, while the scope of the invention is set forth in the claims that follow.

We claim:

1. A fixation device for engaging tissue comprising:
   a mounting body including a stud;
   a first gripping element and a second gripping element mounted to the mounting body, at least one of the first and second gripping elements operably coupled with the stud and adapted to engage tissue therebetween, wherein the first gripping element is movable, in relation to the second gripping element, between a first position wherein the first gripping element and the second gripping element are spaced apart a first distance and a second position wherein the first gripping element and the second gripping element are spaced apart a second distance smaller than the first distance; and
   a coupling device coupled with the mounting body, the coupling device joined to a coupling wire by a frangible portion wherein the frangible portion is configured to detach the coupling device from the coupling wire when a threshold tension force therebetween is exceeded.

2. The fixation device of claim 1, wherein the coupling wire, the coupling device, and the frangible portion, collectively, comprise a single wire.

3. The fixation device of claim 2, wherein the mounting body includes a port to receive the coupling device.

4. The fixation device of claim 2, wherein the single wire includes a zip tie.

5. The fixation device of claim 2, wherein the mounting body includes an opening to slidably receive the wire coupling device.

6. The fixation device of claim 1, wherein the coupling device includes a wire portion of the single wire that has a first end and a second end, the first end being immovably attached to the mounting body.

7. The fixation device of claim 1, wherein the mounting body is slideable relative to the stud;
   the fixation device further including an actuating bar pinned at a first end to the first gripping element to move the first gripping element, in relation to the second gripping element, between the first position, and the second position.

8. The fixation device of claim 7, wherein a second end of the actuating bar is pinned to the stud.

9. The fixation device of claim 8, wherein movement of the stud relative to the mounting body moves the actuating bar.

10. The fixation device of claim 2, wherein the frangible portion includes a length of the single wire having a thickness less than a thickness along a remaining length of the single wire.

11. The fixation device of claim 1, further including a locking mechanism operatively associated with the stud and configured to lock the first gripping element and the second gripping element in at least one of the first position or the second position.

12. The fixation device of claim 1, wherein the coupling device is configured to couple the fixation device to a second fixation device.

13. The fixation device of claim 11, wherein the mounting body is slideable relative to the stud, and the locking mechanism comprises an outwardly projecting member on the stud adapted to engage a mating recess formed on the mounting body.

14. The fixation device of claim 13, wherein the mounting body has a series of mating recesses, each mating recess being adapted to receive and hold the outwardly projecting member of the stud.

15. The fixation device of claim 11, wherein the locking mechanism is configured to allow repeated movement from a locked position to an unlocked position during placement of the fixation device.

* * * * *